United States Patent [19]
Whitehouse et al.

[11] Patent Number: 5,306,412
[45] Date of Patent: Apr. 26, 1994

[54] METHOD AND APPARATUS FOR IMPROVING ELECTROSPRAY IONIZATION OF SOLUTE SPECIES

[75] Inventors: Craig M. Whitehouse; John B. Fenn, both of Branford; Shida Shen, Durham; Cawthon Smith, Norwalk, all of Conn.

[73] Assignee: Analytica of Branford, Inc., Branford, Conn.

[21] Appl. No.: 46,379

[22] Filed: Apr. 8, 1993

Related U.S. Application Data

[63] Continuation of Ser. No. 703,506, May 21, 1991, abandoned.

[51] Int. Cl.⁵ .................. G01N 27/26; G01N 27/447; H01J 49/04; H01J 49/10
[52] U.S. Cl. ................... 204/299 R; 204/180.1; 250/288; 250/423 R; 250/423 F
[58] Field of Search .............. 204/299 R, 180.1; 250/423 F, 423 R, 288; 239/708, 102.2

[56] References Cited

U.S. PATENT DOCUMENTS

| | | | |
|---|---|---|---|
| 4,570,068 | 2/1986 | Sakairi et al. | 250/288 |
| 4,667,100 | 5/1987 | Lagna | 250/288 X |
| 5,157,260 | 10/1992 | Mylchreest et al. | 250/423 R |

FOREIGN PATENT DOCUMENTS

57-53052  3/1982  Japan ............... 250/423 R

*Primary Examiner*—John Niebling
*Assistant Examiner*—John S. Starsiak, Jr.
*Attorney, Agent, or Firm*—Levisohn, Lerner & Berger

[57] ABSTRACT

The subject invention teaches the use of mechanical vibration to enhance the electrostatic dispersion of sample solutions into the small, highly charged droplets that can produce ions of solute species for mass spectrometric analysis. Such vibration turns out to be surprisingly effective at ultrasonic frequencies for solutions with flow rates, conductivities and surface tensions too high for stable dispersion by electrostatic forces alone as in conventional electrospray ionization. Several embodiments of the invention are described for purposes of illustration. Other possible embodiments will become apparent to those skilled in the art.

112 Claims, 14 Drawing Sheets

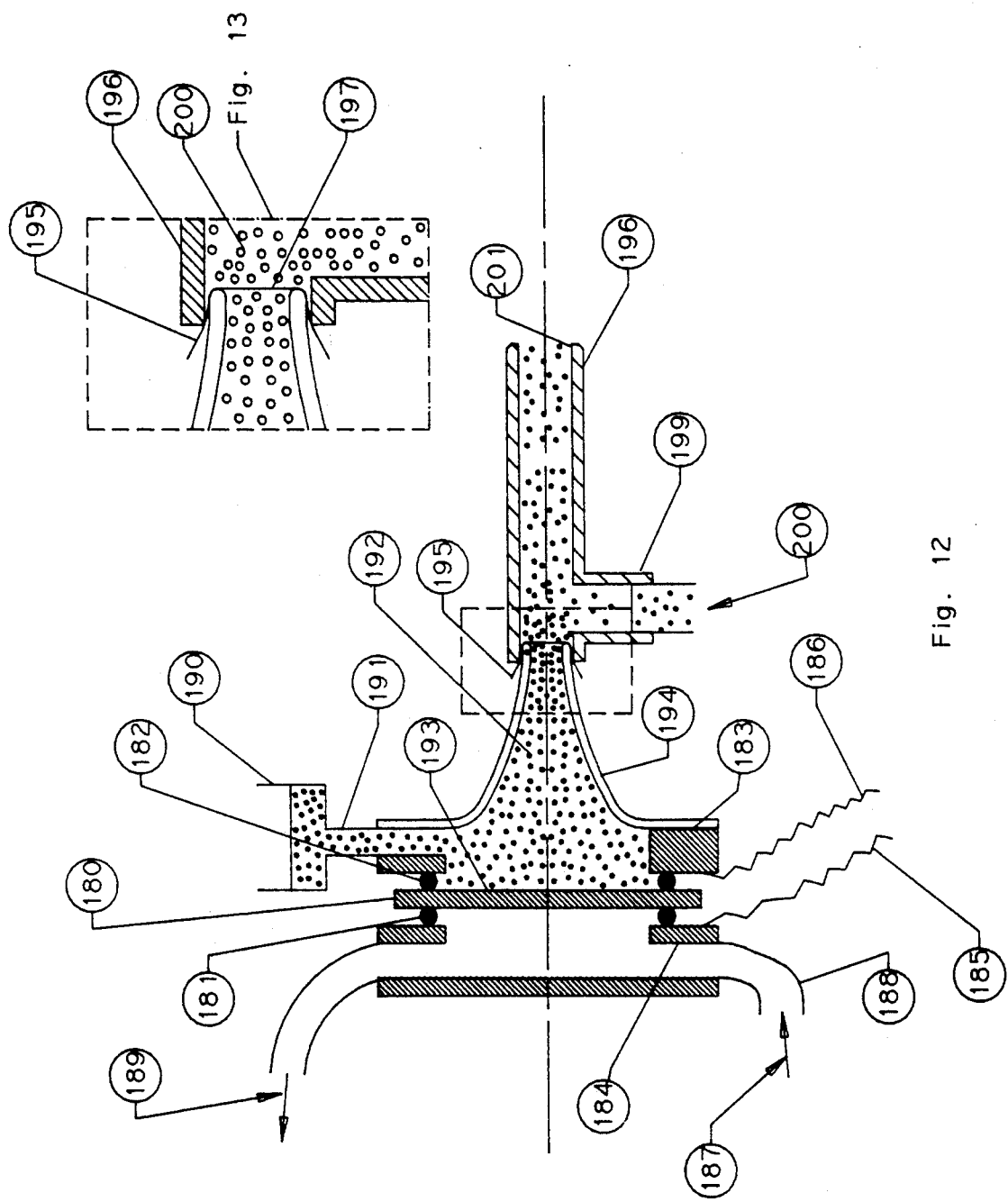

METHOD AND APPARATUS FOR IMPROVING ELECTROSPRAY IONIZATION OF SOLUTE SPECIES

This application is a continuation of application No. 07/703,506, filed May 5, 1991, now abandoned.

BACKGROUND OF INVENTION

Mass spectrometers generally embody two primary components, an ion source that transforms species to be analyzed into ions in vacuum, and a mass analyzer that "weighs" these ions by measuring the response of their trajectories to some combination of electric and magnetic fields. For many years after their introduction, the use of such mass spectrometers was limited to species that were sufficiently volatile to be vaporized so that their dispersed molecules could be ionized by gas phase encounters with electrons, photons, other ions or electronically excited atoms. Non-volatile species could not be turned into ions by such gas phase encounters and therefore could not be individually weighed by ion mass analyzers. Thus, a long standing challenge in chemical analysis has been to extend the powers of mass spectrometric analysis to species that were so large and/or fragile that they could not be vaporized without substantial, even catastrophic, decomposition. In response to this need a number of methods have been developed in the past decade or two that are remarkably capable of transforming intact molecules of complex and fragile non-volatile species from a condensed phase into ions in vacuum ready for mass analysis. Among the most powerful and popular of these "soft" techniques is so called "Electrospray (ES) Ionization." It has been described at length in several U.S. Pat. Nos. (Labowsky et. al., 4,531,056; Yamashita et. al., 4,542,293; Henion et. al., 4,861,988, and Smith et. al., 4,842,701 and 4,885,706) and recent review articles [Fenn et. al., Science 246, 64 (1989); Fenn et. al., Mass spectrometry reviews 6, 37 (1990); Smith et. al., Analytical Chemistry 2, 882 (1990)]. To put the present invention in an perspective it will be appropriate to provide the following brief description of the method.

ES ionization as now practiced generally consists in flowing sample liquid comprising analytical species in a volatile solvent, at a rate typically between 1 and 20 microliters per minute, through a small metal capillary tube into a chamber containing bath gas at or near atmospheric pressure. An electrostatic potential difference of several kilovolts between the needle and the walls of the surrounding chamber produces an electric field at the needle tip that disperses the emerging liquid into a fine spray of charged droplets. Driven by the field toward the end wall of the chamber the droplets shrink by evaporation of solvent and, by a mechanism not yet clearly understood, produce free ions of the solute species in the ambient bath gas. Some of these ions become entrained in a small flow of bath gas through an aperture in the end wall leading into a vacuum system containing a mass analyzer. A most attractive feature of the ES technique is its "softness." Even the most fragile and complex species undergo little or no decomposition. Another attractive feature is that when the solute species comprise large polar molecules, for example biopolymers such as proteins, the ions produced by ES are multiply charged, roughly in proportion to their molecular weight. The result is that their mass/charge (m/z) values are usually less than 2500 or thereabouts so that they can be weighed by relatively inexpensive analyzers. Thus, ES ions of proteins with molecular weights of 130,000 have been accommodated by simple quadruple mass filters because they carry 100 or more charges. Indeed, from intact poly (ethylene oxide) oligomers with molecular weights up to 5,000,000 ES has produced ions with 4,000 or more charges!

In spite of these successes the ES technique is not without problems. Since the work of Vonnegut and Neubauer (Journal of Colloid Science 7, 616 (1952) it has been realized that stable sprays are difficult and sometimes impossible to obtain at atmospheric pressure with solutions having high electrical conductivities, especially when the solvent is mostly water. Moreover, the quality of the spray deteriorates when flow rates through a single needle exceed about 15 to 20 microliters/minute, depending upon the liquid properties. This loss of quality is reflected in poor spray stability and droplets that are too large and polydisperse in size. Another problem stems from the fact that with lower conductivity solutions the total spray current, i.e. flux of charge, is almost independent of the liquid flow rate. Consequently, increasing the flow rate decreases the charge/mass ratio in the droplets formed and, therefore, analytical sensitivity. These constraints complicate the use of ES sources with upstream sample processing such as liquid chromatography (LC) and capillary zone electrophoresis (CZE). Such separation techniques, and other sample treatments that may be desirable, have their own requirements for liquid composition so that compatibility with ES ionization can become difficult to achieve unless the ES step can be made less restrictive in its requirements.

Methods have been developed and applied that can overcome some of these difficulties. The teachings of the Henion patent mentioned above resurrect a technique tried years ago by Malcolm Dole's group [L.L. Mach et. al., Journal of Chemical Physics, 52, 4977 (1970)] and a technique used by the Fenn group from Yale University as shown in U.S. Pat. No. 4,531,056 listed above. Dole's group passed an aspirating gas in an annular flow around the liquid emerging from the injection needle in the hope that ES performance might be improved. They found instead that ion currents decreased so they abandoned further use of the technique. The Fenn group passed an annular gas flow around the liquid emerging from the injection needle to help stabilize the Electrospray particularly in the negative ion producing mode. Nearly 20 years after Dole's work, Henion's group discovered that this "pneumatic assist" allowed them to obtain adequately stable sprays at liquid flow rates as high as 100 or so microliters/minute, higher than unassisted ES can be run with optimal performance. Although these high liquid flow rates exact a penalty in terms of decreased sensitivity, this cost is sometimes sufficiently offset by the convenience of being able to work with sample solutions at flow rates encountered in liquid chromatographic separations. It also turned out that this pneumatic assist could provide acceptable spray stability with liquids that present difficulties in unassisted ES because properties such as electrical conductivity or surface tension are outside the range of optimal performance.

Another strategy that can be used for overcoming composition problems in the liquid is the "sheath flow" technique for use with Capillary Zone Electrophoresis interfacing with Electrospray Ionization taught in the R. D. Smith patent mentioned above. It introduces a second liquid having appropriate properties in annular or sheath flow around a core flow comprising the sample liquid emerging from a dielectric tube. Rapid mixing of the sheath and core flows at the needle tip produces a liquid whose composition is such that it can give rise to a stable ES spray of acceptable quality without the need for any pneumatic assist. This sheath flow technique was extended to running higher conductivity solutions with high aqueous content used typically in liquid chromatography solutions by Whitehouse et. al. (J., proceedings of the 38th Conference on Mass Spectrometry and Allied Topics, P427, (1990)). However, the technique does not significantly extend the range of liquid flow rate.

Even though these approaches have substantially expanded the range of composition and flow rates in liquids, each has compromises in convenience or sensitivity or range of operation. The present invention provides another approach to the sprayability problem that seems to overcome many if not most of the difficulties encountered the techniques of the prior art. Our experimental studies of electrospray dispersion revealed that one of the possible reasons for the difficulties in spraying liquids with high conductivity was that such liquids show an enhanced stability against break up into droplets. Microscopic examination of the tip region of a small tube at a potential of several kilovolts relative to nearby surfaces shows that the meniscus of the emerging liquid assumes a shape approximately that predicted by G. I. Taylor (Proceedings of the Royal Society A313, 453 (1969)) and since known as a "Taylor Cone." Emerging from the tip of this cone is a small filament or jet of liquid that breaks up into tiny droplets within a few jet diameters when the liquid is well-behaved in the sense that it forms a stable spray. When the liquid is highly conductive it does not break up as rapidly. Indeed with the right combinations of voltage and flow rate we could make the jet persist for a distance of over ten centimeters. One possible explanation for this somewhat surprising behavior emerges from a consideration of what happens when the surface of a jet is perturbed by undulations. Rayleigh showed long ago (Proceedings of the Roy. Soc., 29, P.71, (1879)) that if the amplitude of such "varicose" waves exceeds a critical value determined by the properties of the liquid, the waves are amplified by surface tension forces until the jet breaks up into droplets. Indeed such surface wave growth is the generally accepted explanation for the widely practiced nebulization of liquids by ejecting them from an orifice or nozzle as a high velocity stream or jet. When the jet is formed from a highly conductive liquid whose surface is charged, it is to be expected that the effective mobility of surface charge will also be high so that the surface potential, due to the surface charge, should at all times have the same value everywhere on the surface. On the other hand, the local electric field associated with such surface potential increases wherever the radius of curvature of the jet surface may decrease. This local increase in electric field decreases the effective value of the local surface tension, thus, damping the growth of the surface waves and inhibiting the break up of the jet into droplets. This picture accounts for the difficulties encountered in the ES nebulization of highly conductive liquids by purely electrostatic forces. It also suggests that these difficulties might be overcome by somehow providing surface perturbations sufficiently strong to overcome the stabilizing effect of the surface tension. We believe that the role of the gas flow in pneumatically assisted ES is to provide just such perturbations. The present invention is based on our discovery that mechanical vibrations provide a particularly effective and convenient source of the needed perturbations. Aqueous solutions with high conductivity can easily be sprayed with this invention when used in conjunction with Electrospray ionization. Ion production performance and subsequent analysis using mass spectrometry is not compromised with solution liquid flow rates even over 400 ul/min.

BRIEF DESCRIPTION OF THE DRAWINGS

FIG. 12 shows an embodiment of the invention in which the transducer oscillations are coupled directly through the liquid to the needle tip.

FIG. 13 shows a detail of the membrane area isolating the sample solution in the embodiment of FIG. 12.

BRIEF DESCRIPTION OF THE INVENTION

Figure 1:
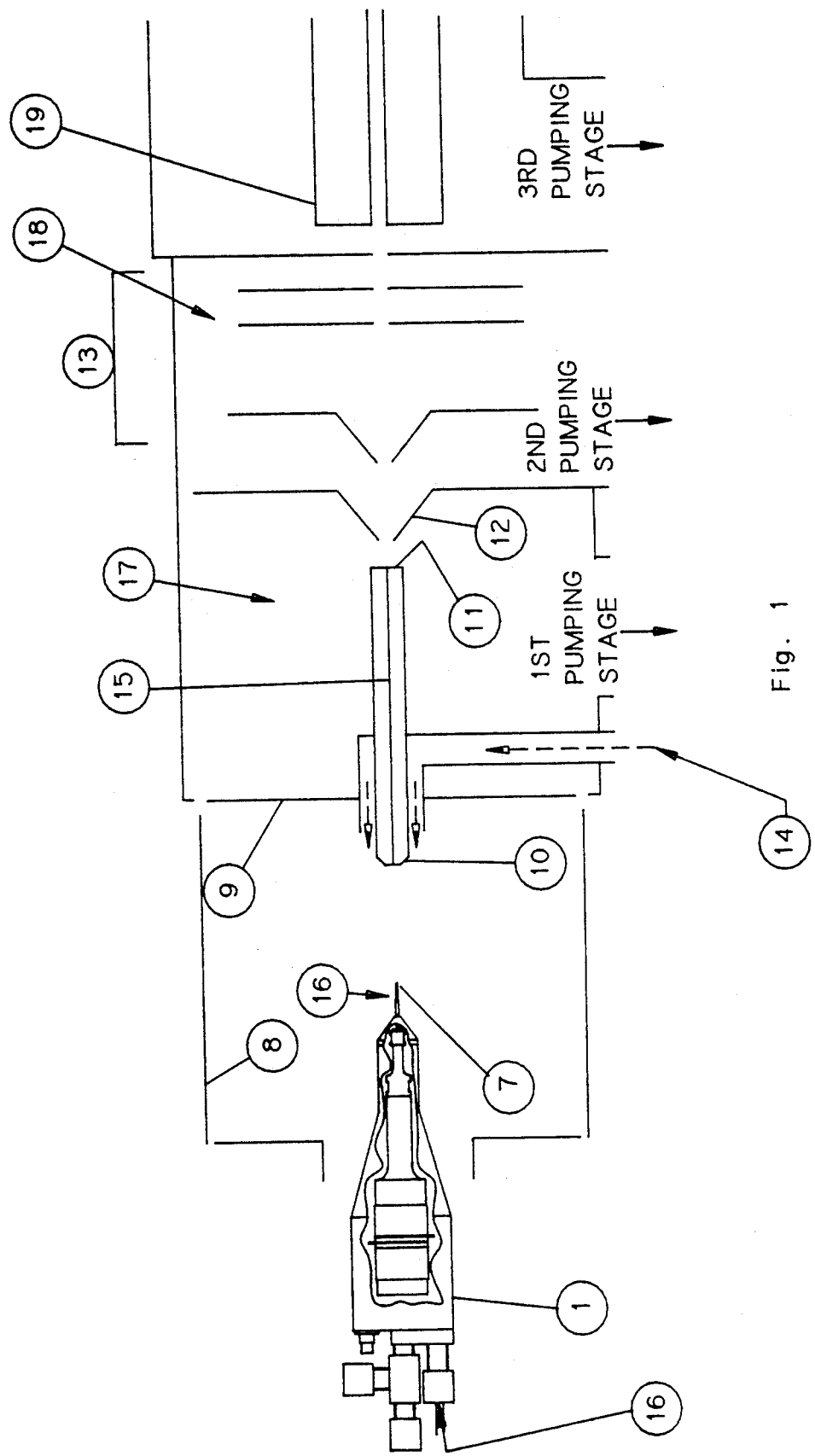
FIG. 1 is a schematic representation of an Electrospray interfaced to a Mass Spectrometer which incorporates one embodiment of the invention.

FIG. 1 shows a schematic representation of an apparatus that embodies the essential features of a typical Electrospray Ion Source interfaced with a quadrupole mass spectrometer. Sample solution at flow rates usually between 1 and 100 μl/min enters the ES chamber through a stainless steel hypodermic needle at ground potential. Typical values of applied voltages for positive ion production are in parenthesis after each of the following components: needle 7 (ground), surrounding cylindrical electrode 8 (−3,000 V), end plate 9 (−4,000 V) metalized inlet 10 (−5,000 V) and exit 11 (+5 to 400) ends of the glass capillary, skimmer 12 (+10), and ion focusing lens 13 voltages ranging from +/− 200 volts. To produce negative ions similar voltages of opposite polarity are applied. In addition, during negative ion production, it is useful to introduce a stream of oxygen or other electron scavenger 16 near the needle tip in order to inhibit the onset of a corona discharge which occurs at lower voltages in the negative polarity mode.

At first glance the indicated potential difference of 5,010 V between the inlet and exit ends of the capillary may seem startling. We have found that with the carrier bath-gas 14 (usually nitrogen) at about 1 atmosphere the ion mobility is low enough so that the gas flows through the capillary inlet and raises the ions back up to ground potential or as much as 15 KV above it. Thus, we can readily provide the energies necessary for injection into a magnetic sector mass analyzer. With this configuration, the sample injection line along with all other external parts of the apparatus are at ground potential and pose no hazard to the operator. Of course, one can replace the glass capillary arrangement with a simple orifice but the ions would not be able to climb electrostatic fields in the free jet. Then the potential of the liquid introduction needle 7 must be raised to a value sufficiently high (usually several kilovolts) to provide the field at the needle tip necessary to disperse the liquid. Because the sample liquid is generally an electric conductor one must also maintain its source at the same potential as the needle, or else provide a power supply with enough capacity to provide the current that flows to ground while maintaining the needle at the desired potential.

The field at the needle tip 7 charges the surface of the emerging liquid which then becomes dispersed by Coulomb forces into a fine spray of charged droplets. Driven by the electric field, the droplets migrate toward the inlet end 10 of the capillary through a counter-current flow 14 of bath gas. As they rapidly evaporate in route, the resulting solvent vapor along with any other uncharged material is swept away from the capillary inlet by the bath gas flow. Meanwhile, in accordance with the scenario described earlier, the rapid evaporation of the migrating droplets promotes the sequence of Coulomb explosions that culminates in the production of droplets small enough to produce solute ions. The ions are entrained in a portion of the bath gas that sweeps through the capillary orifice 15 and enter the first vacuum pumping stage 17 via a free jet expansion. A core portion of this free jet passes through a skimmer 12 into a second vacuum chamber 18, delivering ions to the analyzer. In FIG. 1 the analyzer 19 is a quadruple mass spectrometer filter but almost any other kind of analyzer can be used. Also any number of pumping stages can be used between the atmospheric pressure electrospray chamber and the analyzer chamber.

As mentioned earlier, it becomes difficult to maintain a stable spray when the electrical conductivity, surface tension, or flow rate of the liquid are too high. The present invention overcomes these problems to a substantial extent by providing mechanical vibration strong enough to cause perturbation and even nebulization of the liquid flow. We have found that this vibrational perturbation can be applied directly to the liquid or to the liquid introduction tube tip which then transmits it to the liquid.

Mechanical vibration, particularly in the ultrasonic frequency range, has been used for nebulizing fluids and for breaking up liquid streams into droplets in a controlled manner as known in the arts. The design and use of tuned horns for sonically disrupting cells in solution is explained in U.S. Pat. Nos. 3,328,610 and 3,524,085. The tapered shaping of the horn amplifies the transducer longitudinal movement at the horn tip thus transmitting enough power to cause cavitation when the vibrating horn tip is emersed into liquid. If a hole is drilled into and through the horn tip, this same ultrasonically tuned horn can be used as a nebulizing nozzle for liquid exiting from the tip orifice. Such nozzles are commercially available with operating frequencies up to 120 KHZ. The ink jet printing industry has made use of imposing ultrasonic vibrations both directly to the liquid and to nozzles through which the liquid passes to create a controlled stream of droplets from an orifice tip as described in U.S. Pat. Nos. 3,596,275 and 3,298,030 and a review of the technology by Heinzl et. al. (Advances in Electronics and Electron Physics, Vol. 65, P.91, Academic Press, 1985).

Charge has been deposited on the emerging liquid droplets from an ink jet nozzle by use of a counter electrode. Charging of the droplets allows dispersion of the ink or electrostatically steering of the droplets when forming a printed dot pattern. Ultrasonic mechanical vibration techniques are also used to nebulize liquid in commercial ultrasonic humidifiers and in Inductively Coupled Plasma (ICP) ion sources like those described by Clifford et. al. (Anal. Chem., vol. 62, P.2745, 1990) for use with mass spectrometry. In these applications neutral liquid droplets are produced by nebulization from direct contact with the ultrasonically vibrating transducer. Dropping liquid on the surface of a tuned horn has also been used to produce neutral liquid droplets used in particle beam sources for mass spectrometry as reported by Ligon et. al. (Anal. Chem., Vol. 62, P. 2573, 1990). Each of these applications involved a particular embodiment of the principle of atomizing a liquid by means of vibration but none of those embodiments meet the needs of an Electrospray ion source to be used for mass spectrometric analysis.

Several requirements must be satisfied if mechanical vibration and the ES process are to be combined for mass spectrometric analysis, many of which are not provided for in the prior art. These requirements include the ability to produce very small, very highly charged droplets of uniform size by the presence of an intense electrostatic field at the point of droplet formation, the ability to accommodate a wide range of liquid flow rates and solution properties such as composition, viscosity, surface tension and electrical conductivity, liquid channels with minimal dead volume but flow areas of sufficient size to prevent plugging, long term stability of operation over a wide range of operating conditions, easily replaceable components such as injection needle tips and the ability to provide sheath flows of various liquids around a core flow of sample solution fluids.

When mechanical vibration is used to destabilize or nebulize the liquid flow in an ES source, the point of droplet formation should be located at the point of highest field gradient imposed by the applied voltages to a needle tip. The high field gradient insures maximum droplet charging which is necessary to produce maximum current of analyte into the mass analyzer. The needle tip from which the liquid is emerging must be relatively sharp to insure a high field gradient at that point. The high field gradient at the electrospray tip draws the emerging liquid into a Taylor cone with liquid issuing from the tip as a fine filament or jet. Because the diameter of this jet is much less than the orifice size through which liquid is injected, unassisted electrospray can produce liquid droplets smaller than can be obtained from a jet issuing directly from that orifice. The distribution of droplet sizes produced by an ideal unassisted ES is very monodisperse and the droplets can be as small as 1 or 2 μm in diameter. If any kind of nebulizing assistance is to be provided, the combination should retain the ability to produce a uniform droplet size distribution with droplet diameters well below 10 μm. Larger droplets will produce ions but with less efficiency and abundance. The droplets generated by mechanical vibration as in ultrasonic disruption or nebulization of liquid emerging from a nozzle or tube can have an extremely uniform, size distribution much more so than in the case of pneumatic methods. We have found that the more uniform droplet size distributions obtained with vibrationally assisted ES give rise to better consistency and analytical sensitivity in ion production for mass spectrometry than do the broader droplet size distribution obtained with pneumatic assistance. The mechanically vibrated inkjet printer configuration cited above (U.S. Pat. Nos. 3,298,030 and 3,596,275) can also eject charged droplets from its nozzle tip but such droplets have diameters roughly the same as the nozzle orifice. Due to plugging problems with orifices smaller than 10 μm or so, the techniques used in ink jet printing are not practical for the production of droplets in the size range required for efficient ion production in the mass spectrometric analysis of solutions. Moreover, liquid flow rates that MS ion sources must handle can range from 0.25 μl/min to over 200 μl/min. A single small orifice diameter would not be effective over such a wide range of flow rates.

In the tuned resonating horn approach to vibrationally assisted ES sufficient power applied to the transducer provides enough mechanical displacement at the tip to nebulize the liquid even in the absence of any electrostatic field. Droplet sizes produced by such nebulization depend on the frequency of vibration, the higher the frequency the smaller the droplet size. The present invention combines mechanical vibration, with electric fields in such a way that droplets much smaller than the orifice through which liquid is introduced. Thus by practicing the invention one can use orifices sizes 100 μm or larger in diameter to produce charged droplets of uniform size with diameters much smaller than the orifice diameter with sufficient vibrational power applied in conjunction to assist the electrostatic field. The practice of the invention can produce highly charged droplets with a uniform size distribution, almost regardless of the flow rate or properties of the liquid. The diameter of those droplets is inversely proportional to the frequency of vibration.

One embodiment of the present invention uses a tuned horn to transmit the transducer vibration to the horn tip. The liquid introduction tube is integrated into the horn tip assembly thus becoming part of the resonant structure. To avoid plugging during running, the bore of this tube is conveniently 100 μm or larger in diameter but smaller bores may be used in practicing the invention. To minimize dead volume, this bore diameter can extend from the tip all the way to the sample source. Tuned horns with small bores of such length cannot readily be fabricated, e.g. by drilling a small hole through the horn itself. In the present invention a liquid introduction tube of desired bore is incorporated into a removable segment of a tuned horn having a relatively large channel through it. This arrangement means that the electrospray needle tip is economically, conveniently replaceable. The outer diameter of the tube tip is small enough to provide the high field necessary for ES dispersion of the liquid with or without assistance by mechanical vibration. The tube material is typically stainless steel for compatibility with many types of solutions but other materials with appropriate acoustical properties can be used. When sheath flows are to be introduced around the sample liquid flow, the sample introduction tube can be located inside the bore of the tube that is mechanically vibrated. In this embodiment, the sample introduction tube can be made from virtually any material such as the fused silica widely used in capillary zone electrophoresis and liquid chromatography techniques.

For practical purposes, the sharp Electrospray tip must be readily replaceable. Embodiments of the invention with replaceable needle tips that allow the transmission of mechanical vibration to the tip and provide a convenient means for connecting one or more liquid flow lines are detailed in later sections. A layered liquid flow embodiment is shown in which two liquids can be introduced in annular flow at the needle tip without affecting the coupling of mechanical vibration assistance to the ES dispersion of the liquid. This "layered flow" is convenient when the primary sample flow is less than 0.25 μl/min and additional flow volume is needed for satisfactory dispersion. A second layer of liquid flow can also be used to mix another solution with the primary sample flow. Such mixing sometimes enhances the ion signal that can be obtained. The solution mixing can also be used to ensure an electrical contact from the sample flow to the metal second layer tube. Provision can also be made for an annular flow of gas directed along the spray axis through a third concentric tube layer at the-needle tip. This gas flow can be used in conjunction with the mechanically assisted electrospray, for example, when oxygen is introduced to suppress corona during negative ionization.

When vibration assistance to ES dispersion is to be used for generating ions for mass spectrometric analysis, it may be desirable to provide a countercurrent flow of drying gas at temperatures up to 100 degrees centigrade or more. The present invention allows for stable long term operation under these temperature conditions. In one embodiment an additional gas flow is introduced so as to flow through the gap between the horn and its outer housing exiting in the same direction as the liquid flow near the needle tip in the layered flow configuration. A housing surrounding the tuned horn is configured such that the gas flow exiting at the needle tip first flows over the tuned horn which effectively warms the gas from the heat generated by the transducers and horn. The gas in turn supplies some measure of cooling to the mechanical vibration horn.

DETAILED DESCRIPTION OF THE INVENTION

The essential features of the present invention set forth above include a combination of mechanical vibration with intense electric fields to produce highly charged droplets as a source of ions. A more detailed description is provided in the following sections.

Figure 2:
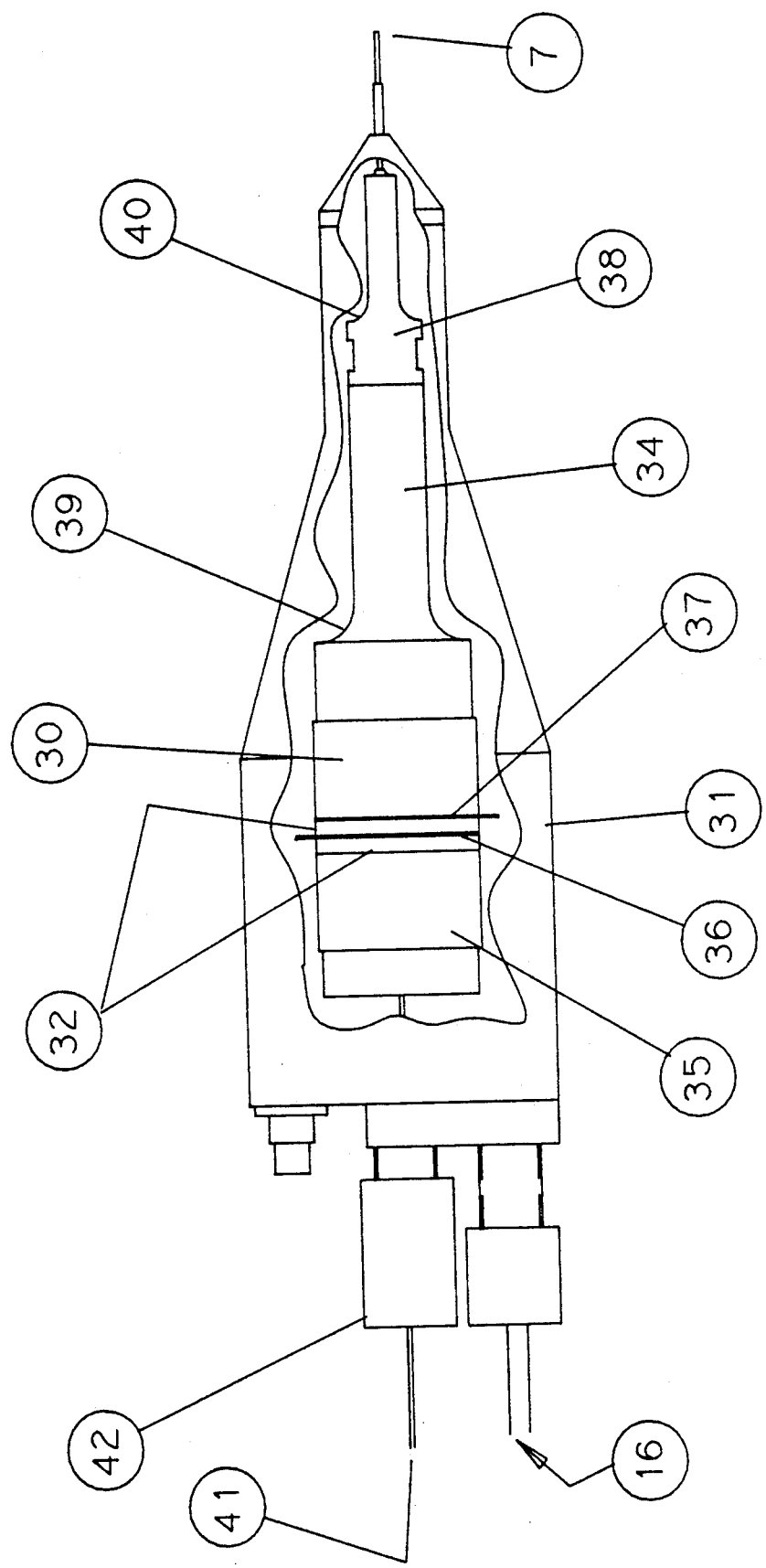
FIG. 2 shows a cutaway drawing of an assembly in which an electrospray liquid introduction needle is vibrated by a tuned horn energized by a transducer.
Figure 3:
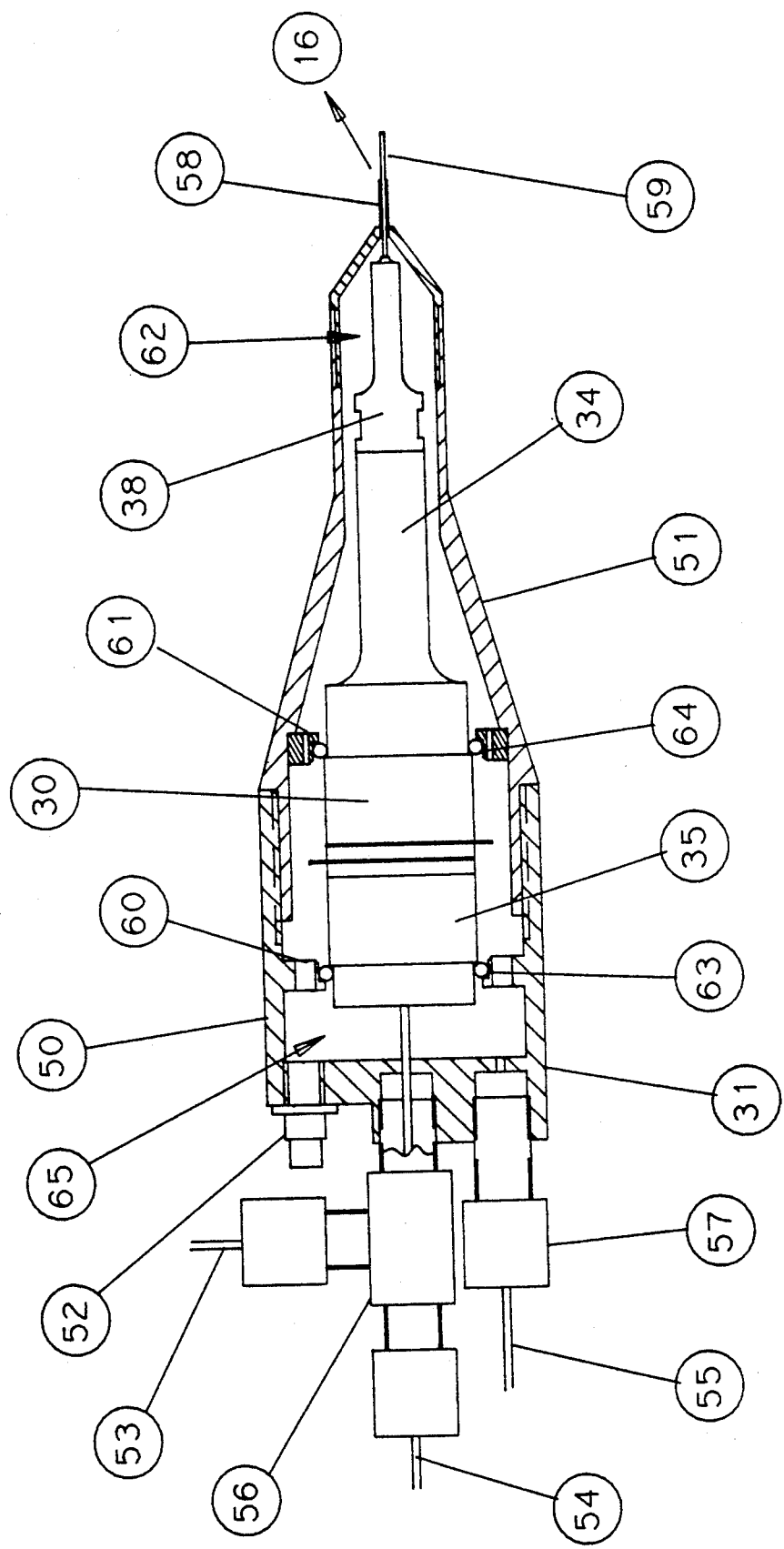
FIG. 3 shows a section view of the embodiment given in FIG. 2.
Figure 4:
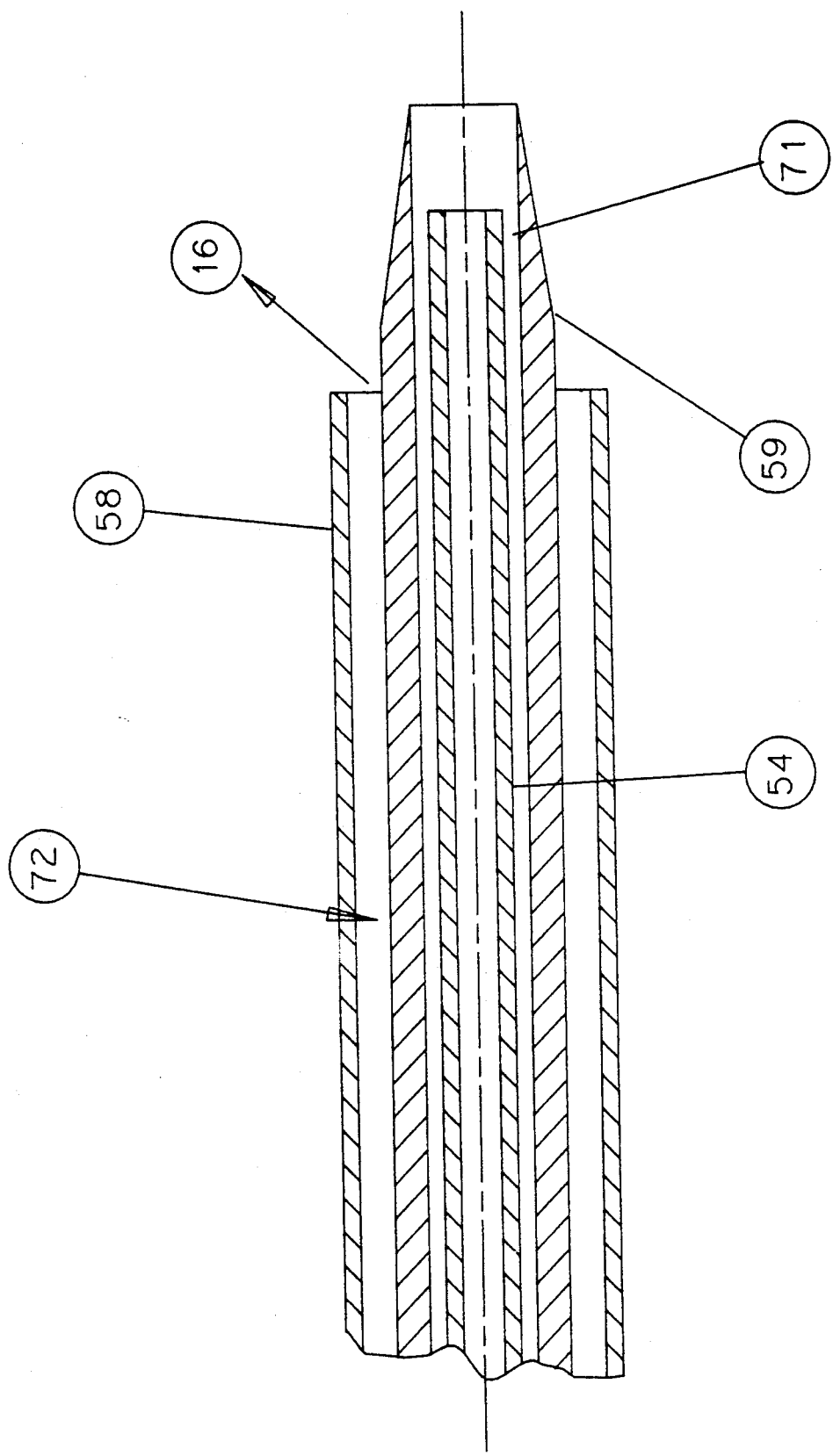
FIG. 4 shows details of the tip of the injection needle assembly of FIG. 3 comprising three concentric tubes.

Shown in FIG. 1 is one embodiment of the invention in which a transducer driven tuned horn is used to vibrate an ES liquid injection needle assembly 1 that is incorporated in an ES ion source for use with a mass spectrometer. Details of this tuned horn assembly 1 are shown in the cutaway drawing of FIG. 2 and the section drawing of FIG. 3. As shown in FIGS. 2 and 3, the tuned horn 30 is mounted inside outer case 31. Piezo crystals 32 with electrical contacts 36 and 37 are sandwiched between a front horn section 34 and a rear section 35. An oscillating voltage is applied across leads 36 and 37 causing the crystals to expand and contract primarily in the horn's longitudinal direction. The longitudinal expansion and contraction of the crystals is transmitted through the horn front section 34 and the removable horn tip 38 into liquid introduction tube and electrospray needle 7. The stepdown in diameter at points 39 and 40 of the front horn section 34 cause an amplification in the piezo electric transducer's longitudinal vibration movement at the electrospray needle tip 7. FIG. 2 shows a two fluid embodiment of the invention that provides a sheath flow layer of a second fluid around a core flow of sample liquid. FIG. 3 shows a three fluid embodiment with two sheath flow layers. Tip details for this configuration are shown in FIG. 4.

In the two fluid embodiment, sample solution enters the injection needle entrance at 41 and travels through to the needle tip 7. Mechanical vibration from the piezo elements 32 is transmitted through the tuned horn to the tip of needle 7. The combination of nebulization or liquid stream disruption and electrostatic potentials applied at the needle tip causes the formation of charged droplets with a fairly uniform droplet diameter distribution. The frequency applied to the crystals is generally that which will match the resonant mechanical frequency to which the horn is mechanically tuned. When sufficient power is applied, the diameter of the droplets created at the horn tip depends on the frequency and power applied with droplet size decreasing with increasing frequency. Increasing power to the crystal at the resonant condition will increase the longitudinal displacement at the needle tip. The oscillating voltage applied to the transducer can be varied to provide the power needed for optimum performance over a wide range of flow rates. Power requirements generally increase with increasing liquid flow rates.

In the embodiment of FIG. 3., the Case or housing 31 surrounding the tuned horn consists of two halves 50 and 51. The rear half 50 supports the feedthroughs for the electrical leads to the piezo crystal 52, the liquid introduction tubes 53 and 54 fitting 56, and fitting 57 for the gas inlet tube 55. The front half of the case 51 forms a conduit for the concentric needle gas flow 16 entering through tube 55 and exiting along the electrospray needle tip through the annulus formed by tubes 58 and 59. During operation, when gas flows through concentric needle 58, the gas enters through tube 55 feeding through fitting 57 into the gap 65 between the horn assembly 30 and the case 31. The gas flows through holes 60 and 61 and into annulus 62. Gas flow through the annular gap between stationary tube 58 and vibrating needle tip 59 exits at the droplet formation area flowing in the direction of the charged liquid droplet movement. The case 31, when assembled, is supported by and held off the horn by two elastic rings 63 and 64 which also serve to reduce contact between the horn and the case. These rings maintain tube 58 concentric with but not touching tube 59 during operation. The ga flowing through the horn and case assembly serves the secondary function of helping to remove heat generated by the piezo transducers and horn during operation. FIG. 4 illustrates the needle tip arrangement where three fluids are used. Sample introduction tube 54, which may comprise a column for separation by Electrophoresis or Liquid Chromatography, lies inside vibrating tube 59 with its exit plane adjustable relative to the exit plane of tube 54. In FIG. 4 the exit plane 54 is shown upstream of tube exit 59. However, in some applications, it may protrude outside the exit plane of tube 59. Tube 58 is a conduit for introducing a third fluid flow 16 through annular space 72. Liquid is introduced through tube 53 which leads through fitting 56 into annular space 71 between tube 54 and vibrating tube 59. The flowing liquid in annulus 71 mixes with or forms a layer on fluid exiting from tube 54. The liquid flowing in annulus 71 may also serve to establish electrical contact with the fluid leaving a tube 54 which may be of dielectric material. Gas 16 introduced through tube 55 and fitting 57 flows into the annular space between tubes 59 and 58 for the third fluid. Placement of the exit plane of tube 58 is adjustable along the axis relative to the exit plane of tube 59.

A two fluid system is shown in FIG. 2. In that configuration tube 54 of the three fluid embodiment is removed and the entrance for tube 59 becomes 41. The bore of tube 59 extends from the tip through fitting 42 with little or no dead volume. FIG. 5 shows horn assembly 30 with the case 31 removed. The front 34 and rear 35 sections of the horn form a sandwich with the transducer crystals 32. The front 34 and rear 35 horn sections, transducer crystals 32 and contacts 36 and 37 are pressed together with bolt 75 through which is bore 79. A removable end piece 38 of the horn is attached to its front section 34 with threaded end 76. The mating surfaces at joint 78 allow transmission of the mechanical vibration from the horn front section 34 into the end section 38. Flats 77 machined into end piece 38 allow simple tightening to the front horn section. The end piece is attached to tube 59 having a small bore by either a press fit or a weld. The mechanical vibration of the end piece 38 is transmitted to tube 59 through the bonded section and thence to the tip 81 causing nebulization or disruption of the exiting liquid flow. Tube 59 in FIG. 5 extends through channel 80 in the horn front section 34 and through channel 79 in bolt 75. Tube 59 can extend an indefinite length beyond the entrance end. Possible dead volume caused by fitting connections have been reduced by passing tube 59 through the horn.

FIG. 6 shows a cross section detail of the horn end piece configuration shown in FIG. 5. Tube 91 is press fit, welded or bonded to the end piece 90 along bore 93. Tube 91 containing a channel most suitable for a given application is shaped at the entrance end 94 to allow attachment to any size tube thus minimizing dead volume at the coupling. Tube 91 is long enough to extend through the channel in horn 30 and bolt 75. The exit end 92 of tube 91 is shaped to maximize the ES performance when Mechanical vibrational assistance is used. Horn endpiece 90 connects to the horn front section by means of threaded portion 95.

FIG. 7 shows an alternative method for attaching a tube to the horn end section so as to allow transmission of mechanical vibration. Tube 104 admits sample solution into end 96 sample introduction needle into the ES chamber at the opposite end 109. It is attached to the horn end piece 100 with a ferrule/nut combination. Ferrule 103 is tightened around needle 104 and end piece face 107 by tightening nut 102 on threaded portion 107. The ferrule may include a longitudinal slit to facilitate compression on tube 104. The nut has an internal taper causing a compression of ferrule 103 along surface 108 when it is tightened. Flat sections on the nut 102 and on the horn end piece 106 facilitate tightening. Mechanical vibration is transmitted through surface 105, ferrule 103 and tube 104 to the exit end 109 Causing liquid flow dispersion or nebulization as liquid emerges into the field. The horn end piece 100 is attached to the horn front section by threaded portion 95.

FIG. 8 shows an alternative to the ferrule arrangement of FIG. 7. A tube 110 is attached to the horn's end piece 111 by a collet section 112 included as part of the end piece. Nut 113 similar to nut 101 of FIG. 7 is tightened onto end piece 111 by threaded portion 115. The internal taper of 114 compresses the longitudinally slit collet 112 of the end piece 111 onto tube 110. Mechanical vibration is transmitted from the endpiece 111 and tube 110 to the exit end 116.

FIG. 9 shows yet another means for attaching removable tip section 120 directly to a removable horn end piece 121. Tube 120 threads into horn endpiece 121 along threaded portion 122 bottoming on surface 129. Channel 128 in the endpiece has a smaller bore than the outer diameter of tube 120 so as to insure a surface contact for transmitting mechanical vibration between the two elements. Tube 125 threads into end piece 121 along threaded portion 126. The exit end 130 of tip 120 Can be shaped to optimize the combination of mechanical vibration in the presence of an electric field for dispersing liquid into charged droplets. Entrance end 127 of tube 125 can be shaped to accommodate a specific fitting type, thus minimizing dead volume. Removable horn section 123 attaches to the front section of the horn by using threaded portion 124. Flat faces 123 are used to grip the horn end piece while tightening.

In any of the embodiments shown in FIG. 6 through 9 the features and shapes of the removable end piece portion can alternatively be included as part of the front horn section. The horn itself can also be fashioned into the shape described for the removable tips and tube pieces and provided with small channels. This approach, however, would not be as convenient or cost effective as the use of replaceable end sections and tips.

FIG. 2 through 9 show a tuned horn configuration in which mechanical vibration is transmitted from vibrating transducers through the horn body to the tip. Mechanical vibration assistance to the electrostatic field dispersion of liquid into charged droplets occurs either by disruption of the jet of fluid issuing from the Taylor cone or by directly nebulizing the liquid off the exit face of the tube. Alternative means are shown in FIG. 10 through 12 whereby the mechanical vibration is applied to the electrospray needle or is conveyed from the vibrating transducer directly into the liquid.

An alternative means for applying mechanical vibration to the ES needle is shown in FIG. 10. Liquid introduction needle 140 is attached directly to vibrating transducer element 141 that is mounted in a cantilever orientation. The transducer is held in place with a double clamp assembly 142 having front 143 and rear 144 clamp sections. These sections are held together with bolts allowing a preset holding force to be applied to the transducer faces. Insulator 148 separates electrode 149 from the clamp face that also serves as the opposing electrode. Alternating voltage is applied to the electrodes through leads 145 and 146 causing the transducer element 141, and the needle tip 147 to oscillate in an axial mode. When this assembly is used in place of assembly 1 in FIG. 1, needle 140 is maintained at potentials up to a few kilovolts relative to the surrounding lenses and the capillary entrance. The needle oscillation in the presence of a strong electrostatic field enhances the formation of charged droplets from the liquid emerging from needle tip 147.

FIG. 11 shows still another embodiment of the invention. Transducer element 160 is mounted in a beam rather than a cantilever configuration. Liquid introduction needle 161 is attached at the center of the edge of the transducer element at point 162. The transducer element is clamped at the edges with back clamp piece 163 and the edge lip 165 of front clamp 164. Electrode 168 is sandwiched in between the back clamp 163 and the transducer 160 along opposite edges. Clamping force is applied between the front 164 and back 163 clamp pieces by bolts 166 and 167. Lead 169 attaches to electrode 168 and lead 170 attaches to front clamp piece 164 that serves as the other electrode. In this embodiment the back clamp piece 163 is dielectric material. Alternating voltage applied to the leads Causes the transducer 160 to oscillate in a direction normal to its free surface. This oscillation in turn causes the liquid injection needle 161 and tip 171 to oscillate primarily in the axial direction. The clamp assembly is attached to rod 172 for mounting in the electrospray chamber. Kilovolt potentials are applied between the needle 161 and the electrospray chamber lenses and capillary entrance while the needle tip 171 is oscillating. This vibrationally assisted ES dispersion can produce relatively mono disperse charged droplets from the liquid leaving needle tip 171. The beam mounted transducer shown in FIG. 11 can achieve a higher Vibration frequency then can be obtained with the cantilever mounting shown in FIG. 10. However, for similar size transducer elements it results in less overall vibrational displacement at the needle tip than the cantilever arrangement. Which configuration may have an advantage for a given application depends on whether one wants more displacement or higher frequency.

FIG. 12 illustrates an embodiment of the invention in which vibration of a transducer is applied directly to the liquid sample being introduced. Transducer 180 is held between rings 181 and 182. The rings are clamped between the front body section 183 and rear body section 184. Electrical leads 185 and 186 attach to opposite sides of the transducer. Alternating voltage applied across the leads causes the transducer faces to oscillate in the surface normal direction. Fluid can be introduced on the rear side of transducer 180 entering at 187 through tube 188 and exiting at 189 for cooling or damping purposes. A static fluid reservoir 190 maintains a constant pressure for fluid entering chamber 192 through conduit 191. The fluid in chamber 192 is in direct contact with the front face 193 of transducer 180. The vibrations imparted to the fluid in chamber 192 by oscillating crystal 180 are transmitted inside of cone 194 through diaphragm 195 into the liquid on the other size.

A detail of the membrane configuration is shown in FIG. 13. Membrane 195 covering the tip of cone 194 creates a seal with tube 196. The oscillating membrane surface 197 imparts its Vibration to the fluid in tube 196 transmitting this Vibration to the sample fluid 198 in tube 196. Sample liquid 200 entering side tee 199 flows through tube 196 to exit 201. Vibration imparted to the fluid through the membrane assists the electric field in forming droplets at needle tip 201. Kilovolt potentials are applied between tube 196 and the surrounding lenses and capillary entrance in the electrospray chamber. The sample fluid exiting from tube tip 201 can be electrosprayed with or without the assistance of the mechanical vibration.

Figure 10:
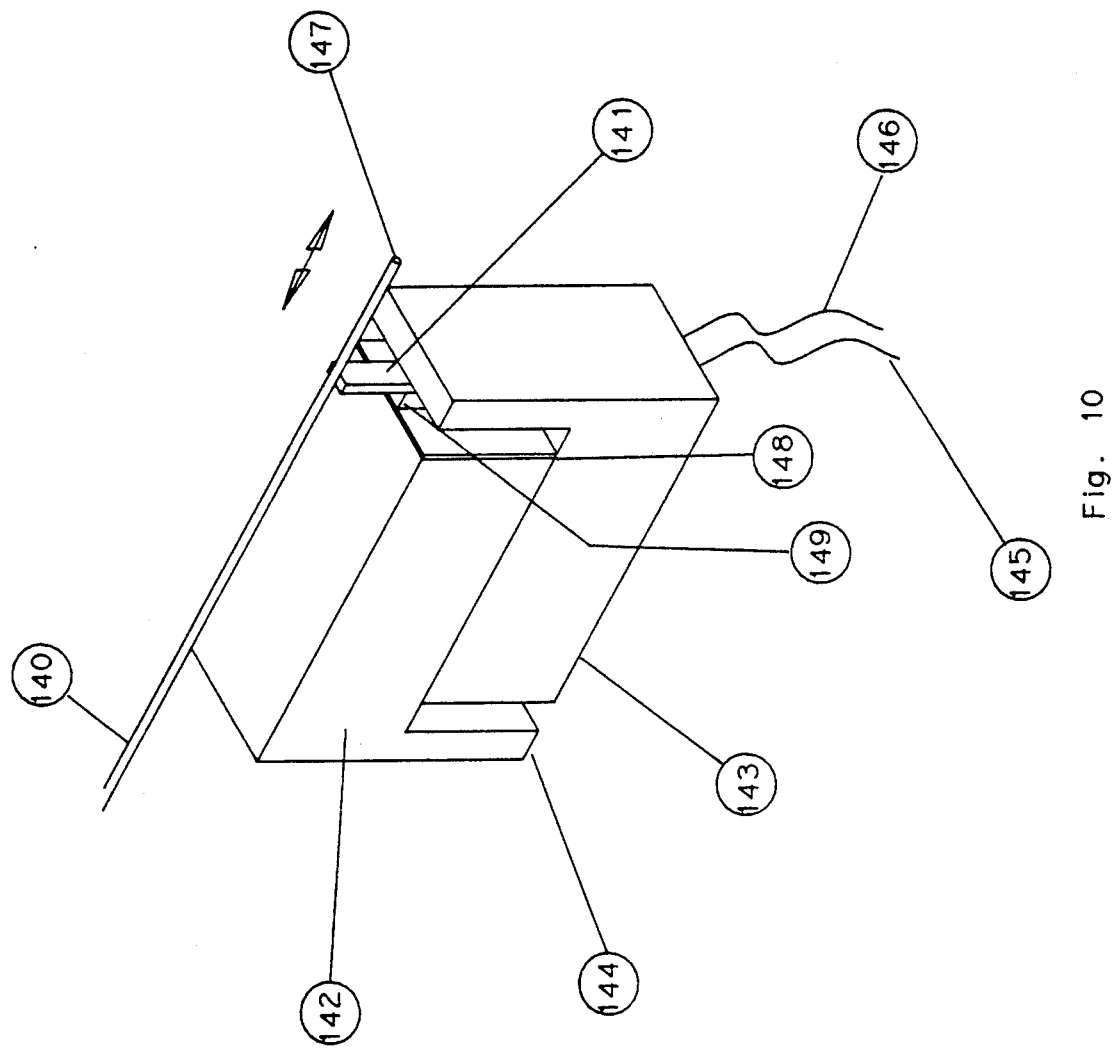
FIG. 10 shows some details of another embodiment of the invention in which the liquid introduction needle is bonded directly to a cantilever vibrating transducer element.
Figure 11:
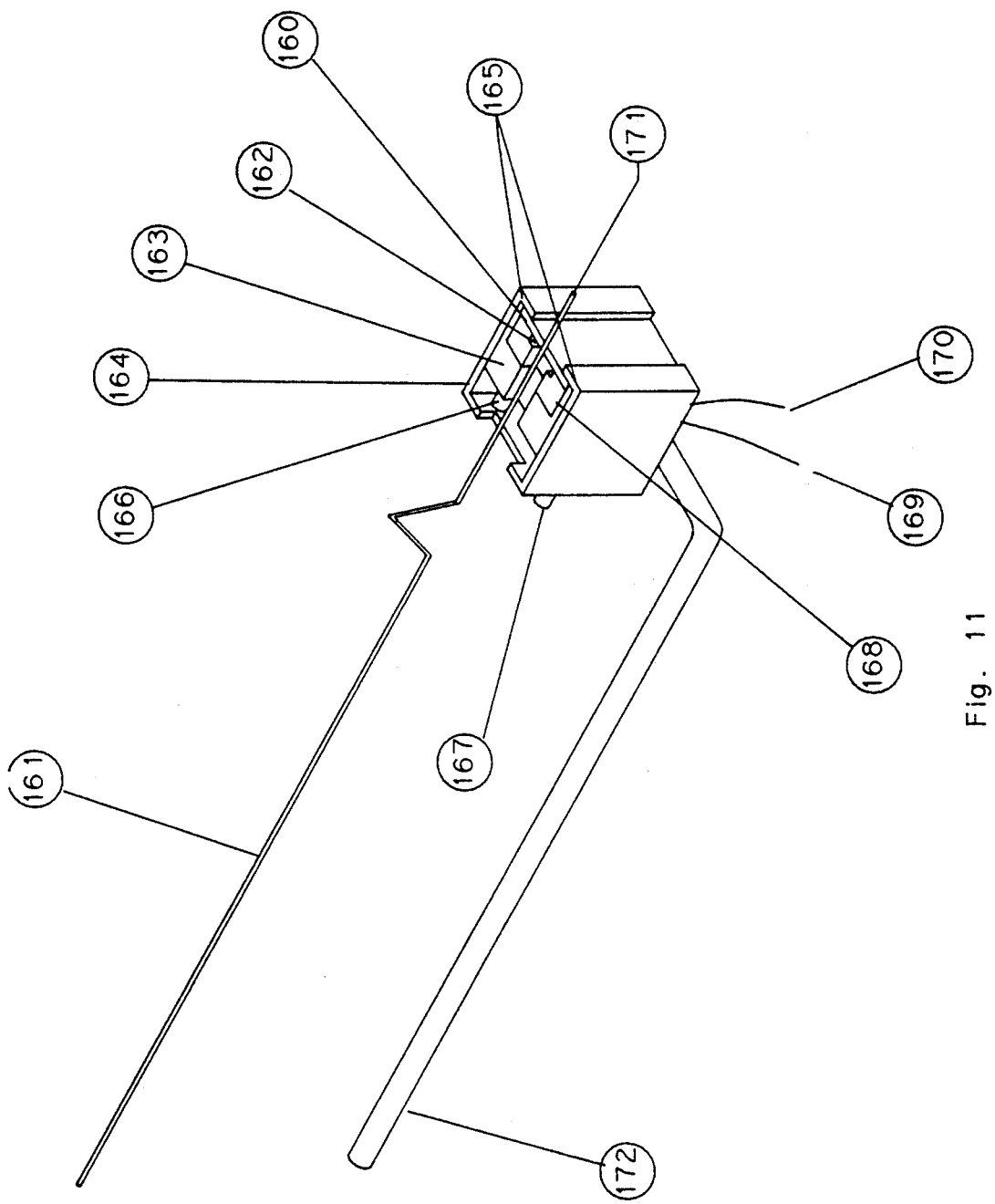
FIG. 11 shows the liquid introduction needle bonded directly to a beam mounted vibrating transducer element.

The embodiments of the essential vibrational feature of the invention in FIGS. 10-12 are variations on the theme shown in FIG. 2. In each case highly charged droplets are produced by the combination of mechanical vibration with electrostatic fields and are driven by the fields in the electrospray chamber towards the entrance of the capillary channel 15 leading into vacuum. Solutions formed from the charged droplets are swept into vacuum through glass capillary tube channel 15 and transported through the vacuum pumping stages to mass analyzer 19. The embodiments shown can also be used to create charged liquid droplets for other analytical methods such as ion mobility analysis and so-called particle beam techniques in mass spectrometry. The mechanical vibration assisted electrospray needle assembly can be used with other configurations of the ES source than is shown in FIG. 1. For example, alternative ES ion source configurations may not include countercurrent bath gas.

Figure 14:
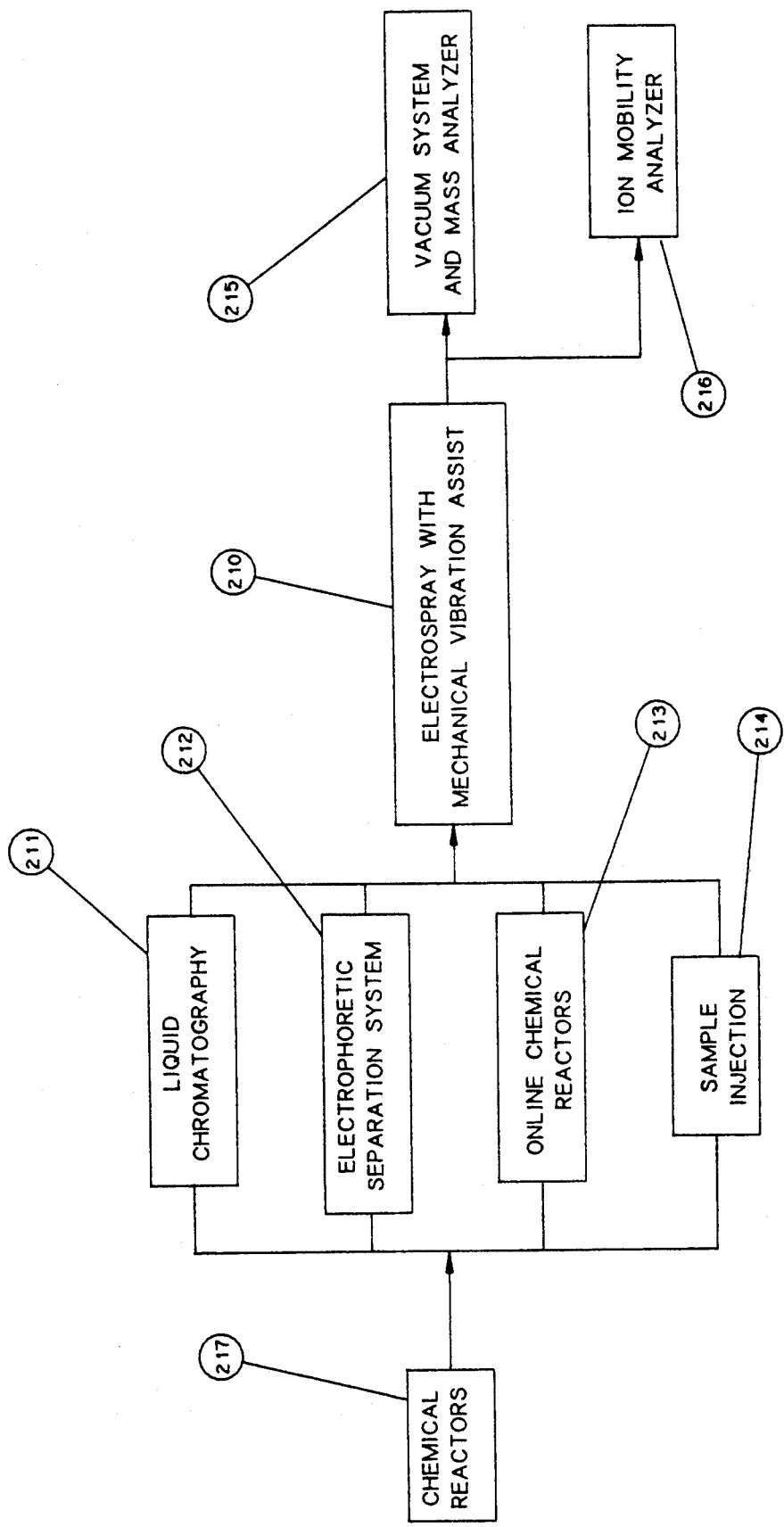
FIG. 14 shows a flow diagram for system comprising a vibrationally assisted electrospray ion source interfaced to a mass spectrometer and a separation or sample reactor system as a source of sample liquid. Also shown is an ion mobility analyzer as an alternative to the mass spectrometer analyzer.

FIG. 14 shows how the invention comprising an ion source 210 based on the combination of electrostatic fields and mechanical vibration to produce charged droplets, can be used to interface an analyzer with any of several sources of sample liquid. The ion source can be interfaced with any one of several possible sample treatment or "front end" systems including a liquid chromatographs 211, electrophoretic separation systems 212, chemical reactors 213 and 217, and direct sample liquid injection inlets 214. The liquids from such sources may be analyzed in this way on an on-line or off-line basis. The analyzing means in such combination may comprise mass spectrometers 215, ion mobility analyzers 216 and photon spectrometers. Clearly, the interfacing possibilities with the vibrationally assisted ES are numerous and not limited to those listed in FIG. 14.

Figure 5:
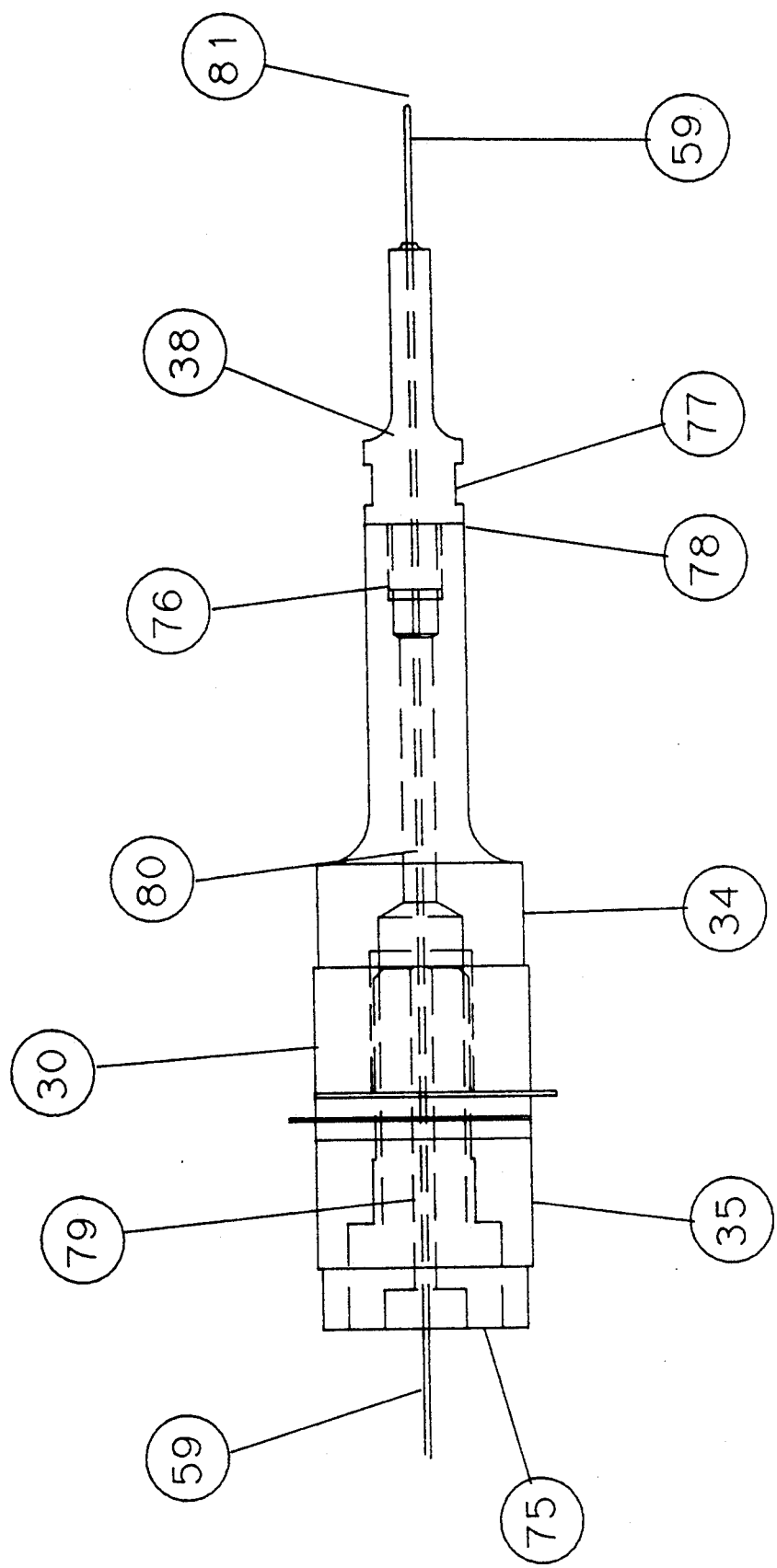
FIG. 5 shows a cutaway drawing of the tuned horn assembly without its housing.
Figure 6:
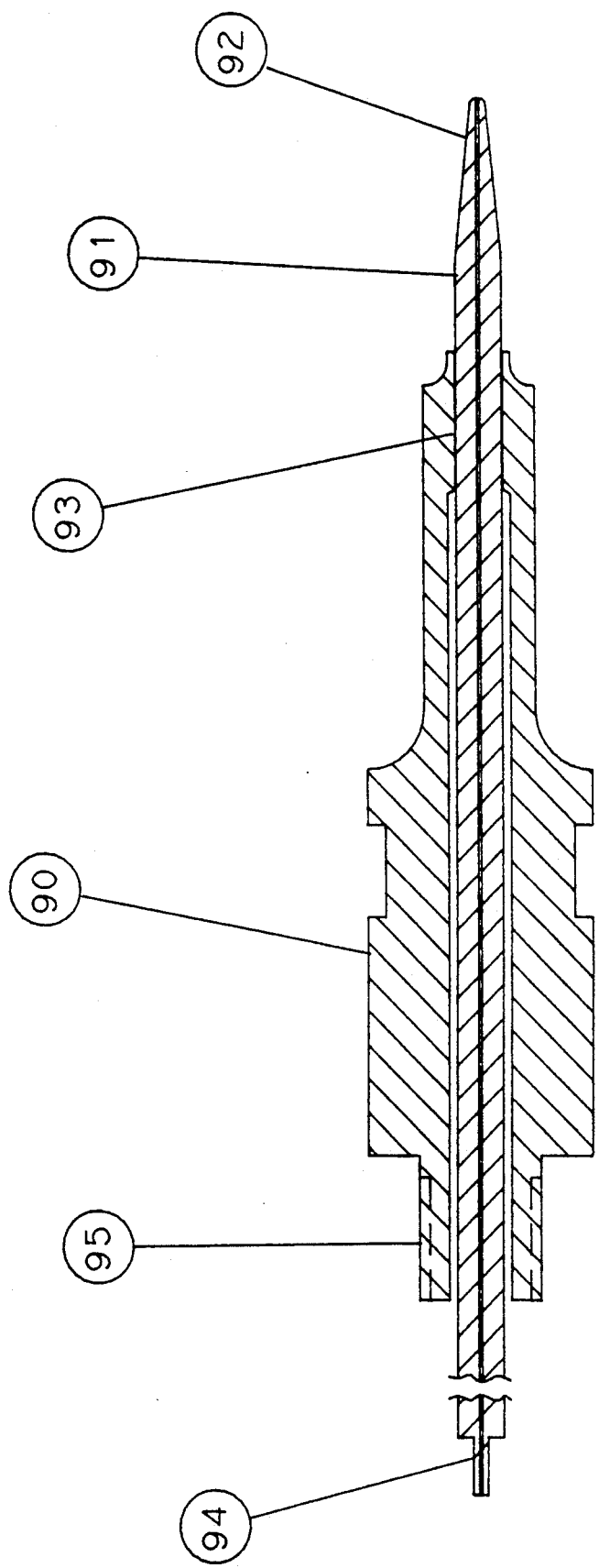
FIG. 6 shows a detail of the liquid exit end piece in which the needle tip is press-fitted or bonded into the removable horn end piece.
Figure 7:
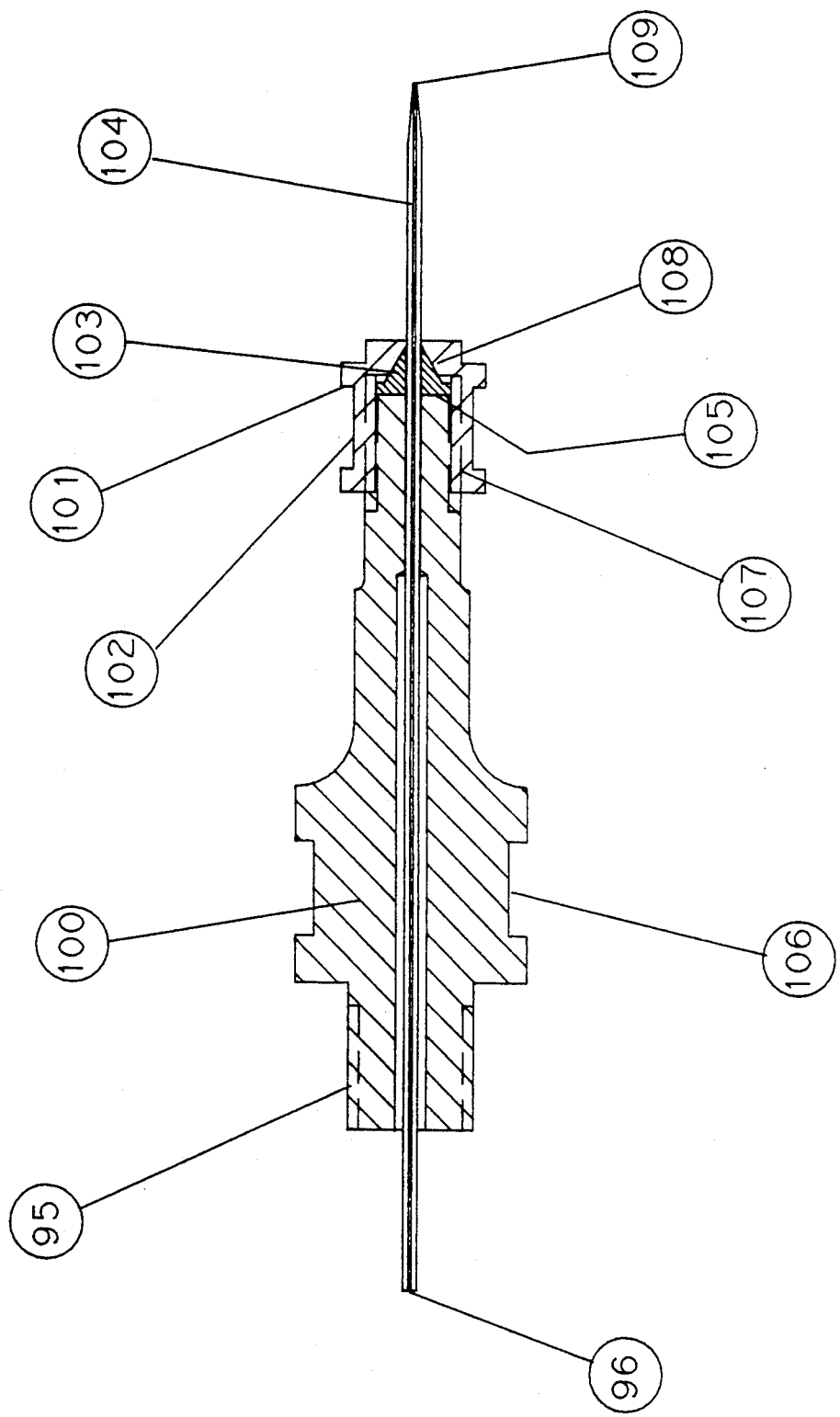
FIG. 7 shows another embodiment of the horn exit end and liquid introduction tube in which the needle tip is connected to the horn end piece by the use of a ferrule and nut arrangement.
Figure 8:
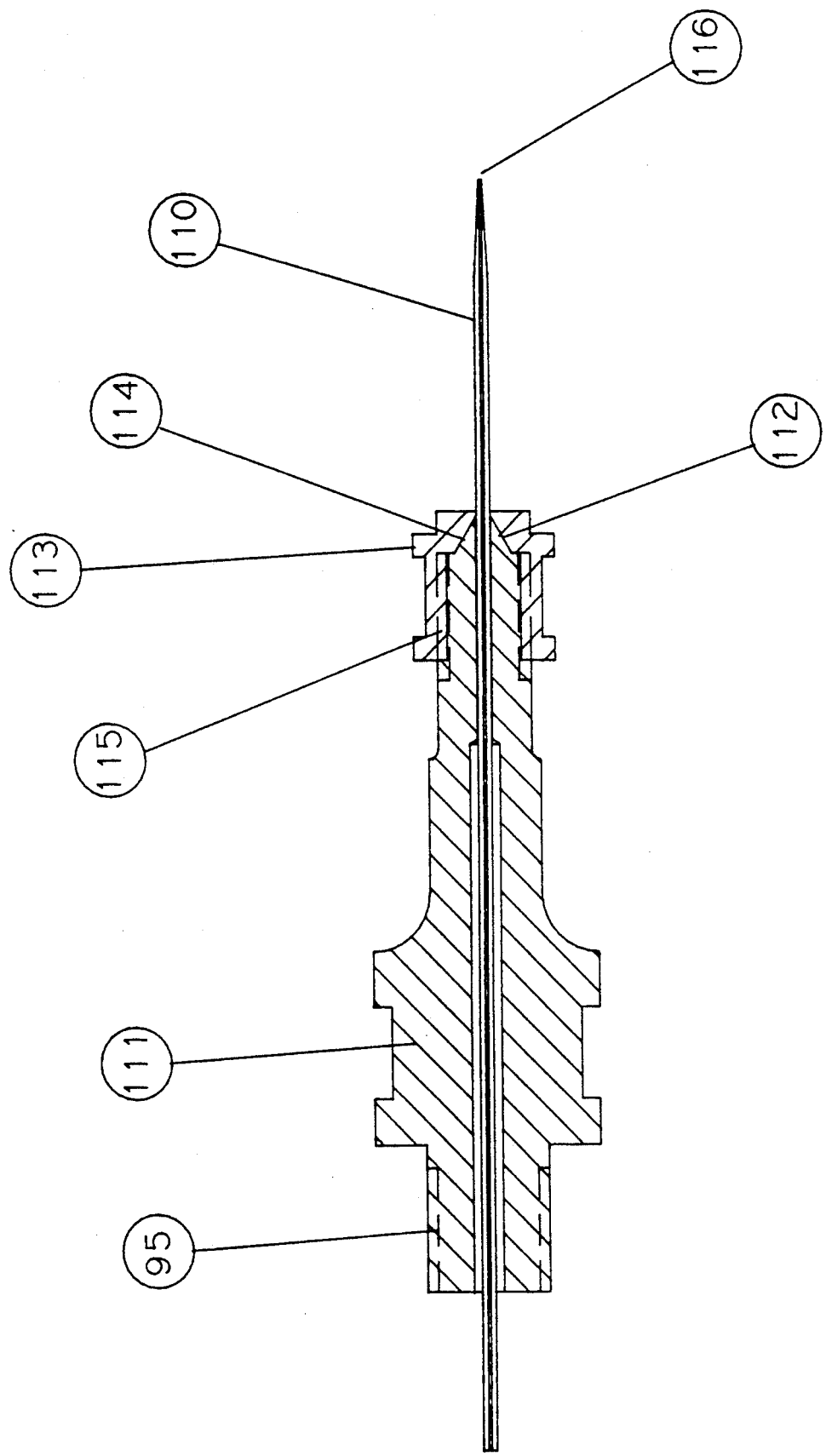
FIG. 8 shows another embodiment of the exit end of the tuned horn in which the horn end piece terminates in a collet and the orifice tip is connected to the horn end with a nut tightened on the collet.
Figure 9:
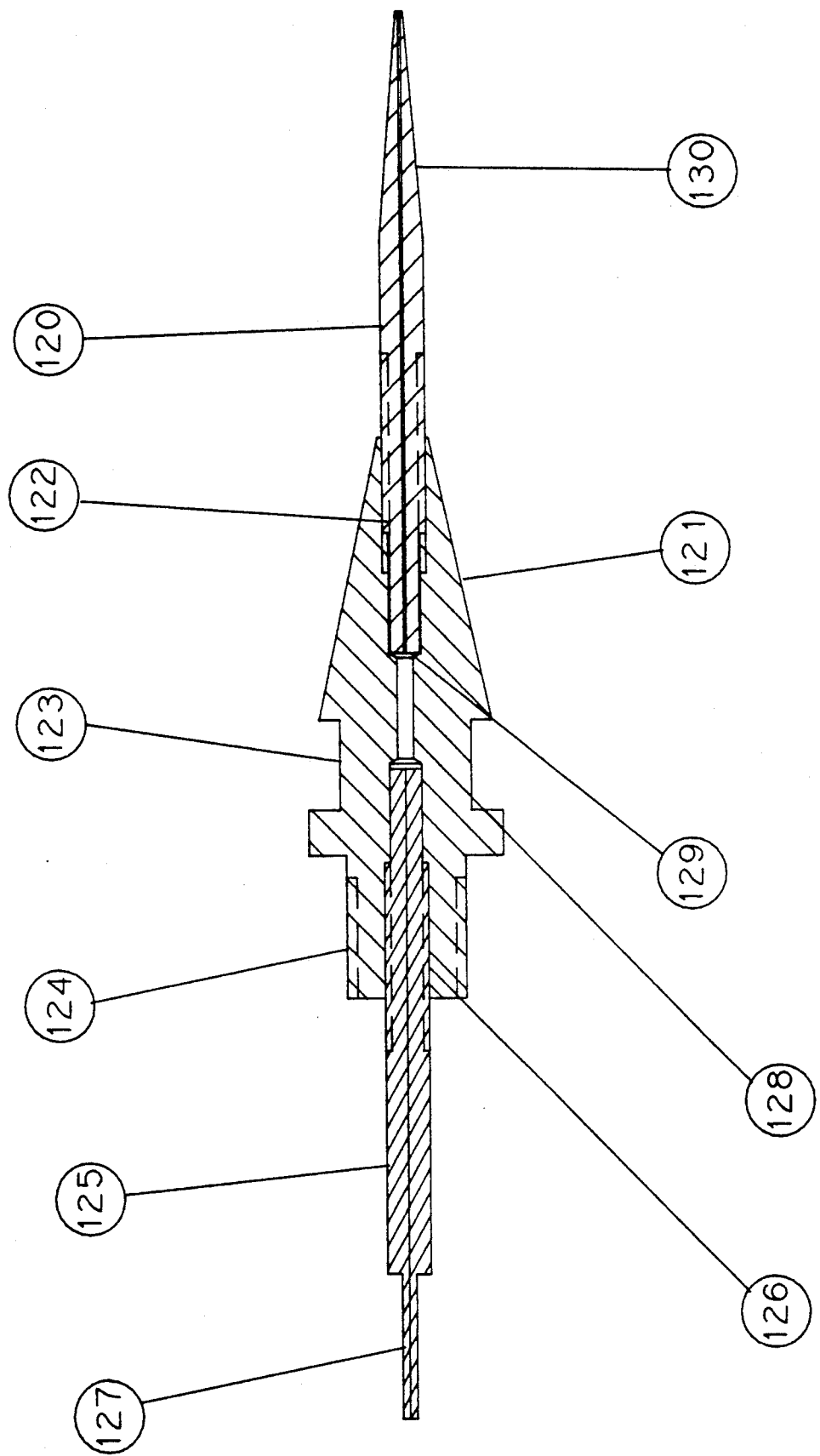
FIG. 9 shows another embodiment of the horn exit in which the tip is threaded directly into the horn.
Figure 15:
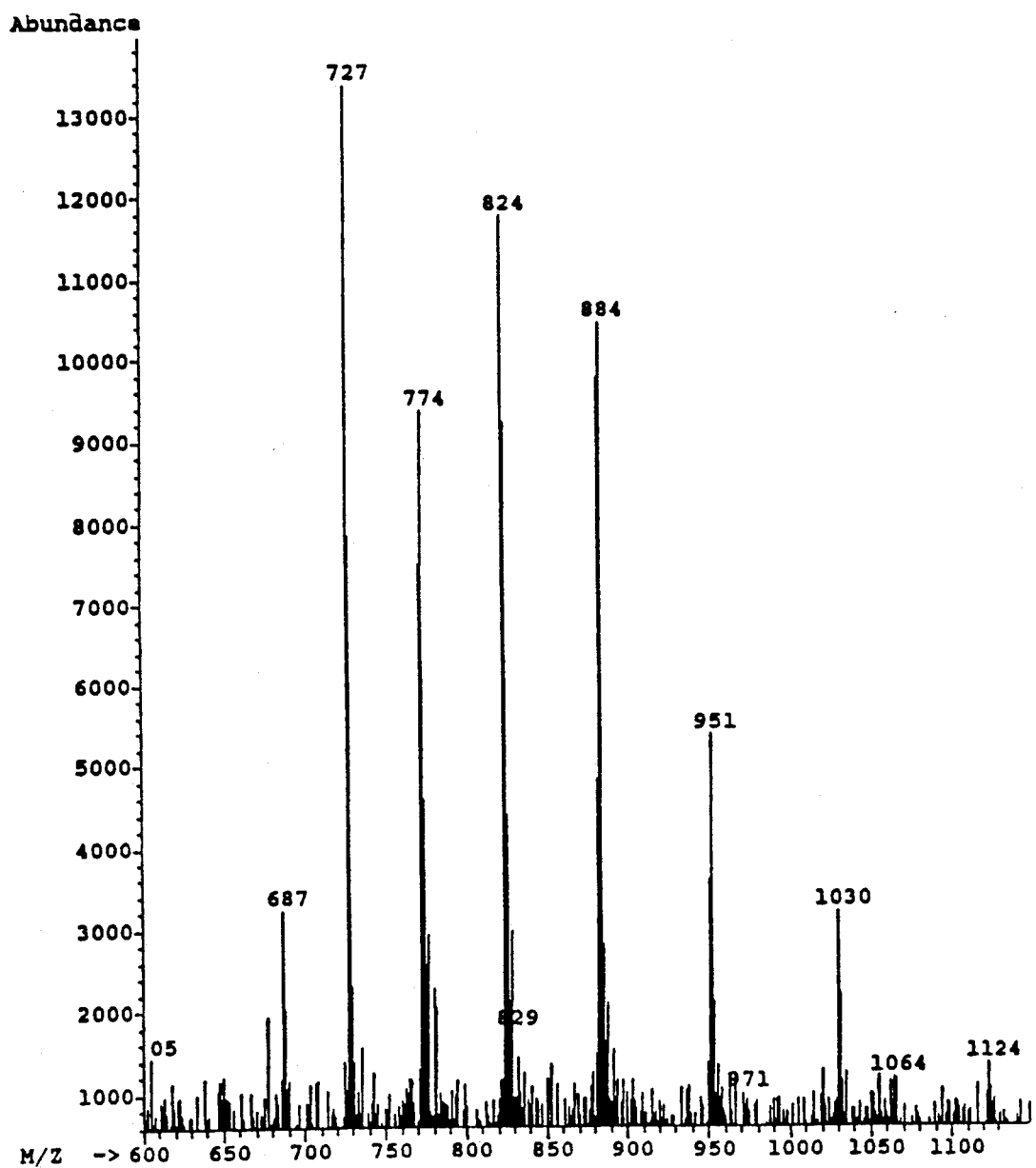
FIG. 15 shows the results of practicing the invention when a solution of Cytochrome C in 1.0% TFA/water infused through the liquid introduction needle into the Electrospray ion source.

FIG. 15 shows a mass spectra obtained by practicing the invention with a solution of Cytochrome C at a concentration of 0.01 μg/ul in 1.0% Trifluoro Acetic Acid (TFA) in water. The spectra is an average of 8 scans of 9 seconds each. The scans were taken with mechanical vibration assisted electrospray using a horn configuration similar to that shown in FIG. 5 with a horn end piece configuration as shown in FIG. 6. The horn was operated at a vibrational frequency of approximately 170 KHz and the liquid flow rate was 4.4 μl/min. No consistent spectra of Cytochrome C could be obtained with this solution when ES dispersion was used without assistance by mechanical vibration. Good quality spectra were obtained only when ES was assisted by mechanical vibration.

It will be clear to those skilled in the art that there are many more assemblies of components than we have shown that embody the essential features of the invention that will be covered by the following claims:

We claim:

1. A method for the production of ions from a liquid sample for analysis of said ions, comprising:

providing a tubular conduit having an exit end, said tubular conduit having a channel of small diameter at said exit end, said exit end serving as the tip of said tubular conduit, passing said liquid sample through said tubular conduit;

maintaining said conduit at an electrical potential at said exit end relative to a conductive surface at some distance from said exit end, said conducting surface serving as a counter electrode to said conduit, simultaneously subjecting said liquid sample to both an electrostatic field and mechanical vibration at the point of exit form said tubular conduit to form charged droplets of said liquid sample at said point of exit and to induce emission of ions from said charged droplets.

2. A method as in claim 1, further comprising the initial step of separating out said liquid sample from a solution comprising one or more of the following: polypeptides, proteins, nucleic acids, oligonucelotides, oligosaccharides, or other biopolymers, biological molecules or biological marcromolecules.

3. A method as in claim 1, further comprising the initial step of separating out component species from an initial solution to produce said liquid sample.

4. A method as in claim 3, wherein said separation is accomplished by liquid chromatography.

5. A method as in claim 3, wherein said separation is accomplished by electrophoresis.

6. A method as claim 1, further comprising the step of supplying said liquid sample from a chemical reactor.

7. A method as in claim 1, further comprising the step of heating said tubular conduit.

8. A method as in claim 1, comprising the step of directly mechanically vibrating said tubular conduit.

9. A method as in claim 1, wherein said mechanical vibration is directly imparted to said liquid sample while said liquid sample is in said tubular conduit.

10. A method as in claim 1, wherein said tip end of said tubular conduit is mechanically vibrated.

11. A method as in claim 1, further comprising the step of adjusting said mechanical vibration to aid the process of formation of said charged droplets.

12. A method as in claim 1, further comprising the step of adjusting the amplitude of said mechanical vibration.

13. A method as in claim 1, further comprising the step of adjusting the frequency of said mechanical vibration.

14. A method as in claim 13, further comprising the step of adjusting the amplitude of said mechanical vibration.

15. A method as in claim 1, further comprising the step of connecting a vibrating transducer to said tubular conduit to apply mechanical vibration to said tubular conduit.

16. A method as in claim 15, wherein said vibrating transducer comprises piezoelectric crystals.

17. A method as in claim 1, further comprising the step of connecting a tuned horn to said tubular conduit to amplify the mechanical vibration applied to said tubular conduit, said tuned horn comprising a body whose cross sectional area at one end is substantially smaller than its cross sectional area at its other end, so that the amplitude of vibration at the end of said tuned horn of smaller cross sectional area is substantially larger than the amplitude of vibration applied to the end of said tuned horn of larger cross sectional area.

18. A method as in claim 1, wherein said tubular conduit comprises at least one annular passage in addition to said channel.

19. A method as in claim 18, further comprising the step of passing a sheath fluid through said at least one annular passage.

20. A method as in claim 19, wherein liquid flows from said tip of said tubular conduit, further comprising the step of layering said liquid flow emerging from said tip of said tubular conduit, so that said sheath fluid and said liquid sample merge as said sheath fluid and said liquid sample emerge from said tip of said tubular conduit.

21. A method as in claim 18, wherein said tubular conduit comprises at least an outermost and at least one inner annular passage around said channel, wherein sheath fluid flows in the outermost annular passage of said tubular conduit and said sheath flow in said outermost annular passage is gaseous.

22. A method as in claim 21, further comprising the step of directing said gaseous sheath fluid is said outermost annular passage at a higher velocity than the velocity of said liquid sample.

23. A method as in claim 21, further comprising the step of directing said gaseous sheath fluid through said outermost annular passage, directing sheath fluid through said at least one inner annular passage, wherein said gaseous sheath fluid in said outermost annular passage is at a higher velocity than the velocities of either said liquid sample or said sheath fluid in said inner annular passages.

24. A method as in claim 21, further comprising the step of cooling said tuned horn using said gaseous sheath fluid.

25. A method as in claim 1, further comprising the step of forming ions from said charged droplets by evaporating solvent from said charged droplets in a bath gas maintained at a substantial fraction of normal atmospheric pressure at sea level.

26. A method as in claim 25, further comprising the step of directing said bath gas countercurrent to the direction of flow of said ions.

27. A method as in claim 25, further comprising the step of directing said ions and bath gas into a vacuum system.

28. A method as in claim 25, further comprising the step of directing said bath gas and ions to be analyzed into a vacuum system comprising said analyzer, said bath gas and ions entering said vacuum system through a tube means of dielectric material whose entrance and exit ends and end faces are electrically conducting so that each end of said tube means can be independently maintained at a desired electrical potential by connection to an electrical power supply means at said tube entrance end and additional electrical power supply means at said tube exit, each said electrical power supply means having variable voltage.

29. A method as in claim 1, further comprising the step of analyzing said ions.

30. A method as in claim 1, further comprising the step of analyzing said ions with a mass spectrometer.

31. A method as in claim 1, further comprising the step of analyzing said ions with a mobility analyzer.

32. A method as in claim 1, further comprising the step of analyzing said ions with a photon spectrometer.

33. A method of analyzing liquid samples which comprises the production of charged droplets from said liquid sample, and the production of ions from said charged droplets, said method comprising the steps of:

flowing a first liquid sample to be analyzed through a first tubular conduit with a small diameter at an exit end so that said first liquid sample emerges from said exit end of said first tubular conduit, flowing a second solution through the annulus between an inner bore of a second tubular conduit and the outer surface of said first tubular conduit, where said first tubular conduit extends through said inner bore of said second tubular conduit, with means to adjust the relative positions of the exit ends of said first and said second tubular conduits, said second solution exiting at the exit end of said second tubular conduit, wherein said second solution mixes with said first liquid sample, maintaining at said exit of said first and second tubular conduits a bath gas, supplying to either said first or second tubular conduit an electrical potential capable of maintaining said exit end of said second tubular conduit at a high potential with respect to some neighboring conductive surface so as to produce a strong electrostatic field at said exit end of said second tubular conduit such that an electric current flows from said second tubular conduit to said neighboring surface when said mixture of liquid sample and second solution is flowing through said second tubular conduit, said electrical current comprising charged droplets and molecular ions driven through said bath gas by said electrostatic field, said charged droplets having been produced by said electrostatic field from said mixture of said liquid sample and second solution as said mixture emerges from said exit end of said second tubular conduit, and said molecular ions having been produced from said charged droplets as they evaporate in said bath gas, providing a means for simultaneously mechanically vibrating said second tubular conduit's exit end at high frequency while it is at high potential relative to said neighboring surface, said mechanical vibration aiding in said charged droplet formation from said mixture as it emerges from said second tubular conduits exit end, and said mechanical vibration aiding in emission of ions from said charged droplets.

passing said bath gas containing said evaporating charged droplets and molecular ions produced from said evaporating charged droplets into an analyzing means for analysis of said ions.

34. A method as in claim 33, further comprising the initial step of separating out said liquid sample from a solution comprising one or more of the following: polypeptides, proteins, nucleic acids, oligonucleotides, oligosaccarides, or other biopolymers, biological molecules or biological marcromolecules.

35. A method as in claim 33, further comprising the initial step of separating out component species from an initial solution to produce said liquid sample.

36. A method as in claim 35, wherein said separation is accomplished by liquid chromatography.

37. A method as in claim 35, wherein said separation is accomplished by electrophoresis.

38. A method as claim 33, further comprising the step of supplying said liquid sample from a chemical reactor.

39. A method as in claim 33, further comprising the step of heating at least one of said tubular conduits.

40. A method as in claim 33, comprising the step of directly mechanically vibrating at least one of said tubular conduits.

41. A method as in claim 33, wherein said liquid sample is directly mechanically vibrated.

42. A method as in claim 33, wherein said second solution is directly mechanically vibrated.

43. A method as in claim 33, wherein said tip end of said tubular conduits is mechanically vibrated.

44. A method as in claim 33, further comprising the step of adjusting said mechanical vibration to aid the process of formation of said charged droplets.

45. A method as in claim 33, further comprising the step of adjusting the amplitude of said mechanical vibration.

46. A method as in claim 33, further comprising the step of adjusting the frequency of said mechanical vibration.

47. A method as in claim 46, further comprising the step of adjusting the amplitude of said mechanical vibration.

48. A method as in claim 33, further comprising the step of connecting a vibrating transducer to said tubular conduit to apply mechanical vibration to said tubular conduit.

49. A method as in claim 48, wherein said vibrating transducer comprises piezoelectric crystals.

50. A method as in claim 33, further comprising the step of connecting a tuned horn to said tubular conduits to amplify the mechanical vibration applied to said tubular conduits, said tuned horn comprising a body whose cross sectional area at one end is substantially smaller than its cross sectional area at its other end, so that the amplitude of vibration at the end of said tuned horn of smaller cross sectional area is substantially larger than the amplitude of vibration applied to the end of said tuned horn of larger cross sectional area.

51. A method as in claim 33, wherein said second tubular conduit comprises at least an outermost and at least one inner annular passage, wherein said sheath fluid in the outermost annular passage of said tubular conduit is gaseous.

52. A method as in claim 51, further comprising the step of passing a gaseous sheath fluid through said outermost annular passage at a higher velocity than the velocity of said liquid sample.

53. A method as in claim 51, further comprising the step of directing said gaseous sheath fluid through said outermost annular passage, directing sheath fluid through said at least one inner annular passage, wherein said gaseous sheath fluid in said outermost annular passage is at a higher velocity than the velocities of either said liquid sample or said sheath fluid in said at least one inner annular passage.

54. A method as in claim 51, further comprising the step of cooling said tuned horn using said gaseous sheath fluid.

55. A method as in claim 33, further comprising the step of directing said bath gas countercurrent to the direction of flow of said ions.

56. A method as in claim 33, further comprising the step of directing said bath gas and ions to be analyzed into a vacuum system comprising said analyzer, said bath gas and ions entering said vacuum system through a tube means of dielectric material whose entrance and exit ends and end faces are electrically conducting so that each of said tube means can be independently maintained at a desired electrical potential by connection to an electrical power supply means at said tube entrance end and additional electrical power supply means at said tube exit, each said electrical power supply means having variable voltage.

57. A method as in claim 33, further comprising the step of analyzing said ions with a mass spectrometer.

58. A method as in claim 33, further comprising the step of analyzing said ions with a mobility analyzer.

59. A method as in claim 33, further comprising the step of analyzing said ions with a photon spectrometer.

60. An apparatus for the production of ions from a liquid sample for analysis of said ions, comprising:
a liquid sample,
providing a tubular conduit having an exit end, said tubular conduit having a channel of small diameter at said exit end, said exit end serving as the tip of said tubular conduit,
maintaining said conduit at an electrical potential at said exit end relative to a conductive surface at some distance from said exit end, said conducting surface serving as a counter electrode to said conduit,
means for simultaneously subjecting said liquid sample to both an electrostatic field and mechanical vibration at the point of exit from said tubular conduit to form charged droplets of said liquid sample at said point of exit and induce the emission of ions from said charged droplets.

61. An apparatus as in claim 60, further comprising separation means to separate out component species from an initial sample to produce said liquid sample.

62. An apparatus as in claim 60, wherein said separation means comprises a liquid chromatograph.

63. An apparatus as in claim 60, wherein said separation means comprises an electrophoretic separation system.

64. An apparatus as in claim 60, further comprising a chemical reactor to supply said liquid sample.

65. An apparatus as in claim 60, further comprising transducer means for providing said mechanical vibration.

66. An apparatus as in claim 65, wherein said transducer means mechanically vibrates at high frequency in response to an applied electrical signal.

67. An apparatus as in claim 65, wherein said transducer means comprises piezoelectric crystals, to which an electrical signal is applied.

68. An apparatus as in claim 65, wherein transducer means is directly in contact with said tubular conduit, so that the vibration of said transducer means is directly imparted to said tubular conduit, said tubular conduit imparting vibration to said liquid sample as said liquid sample exits from the exit end of said tubular conduit.

69. An apparatus as in claim 65, wherein said vibrating transducer is directly in contact with said liquid sample so that the vibration of said transducer means is directly imparted to said liquid sample, which liquid sample vibrates at said exit end of said tubular conduit.

70. An apparatus as in claim 65, wherein said transducer is coupled to a tuned horn, said tuned horn comprising a tapered body whose cross sectional area at one end is substantially smaller than the cross sectional area at its other end, so that the amplitude of vibration at the end of said tuned horn of smaller cross sectional area is substantially larger than the amplitude of vibration applied to the end of said tuned horn of larger cross sectional area.

71. An apparatus as in claim 70, wherein said tuned horn is coupled to said tubular conduit.

72. An apparatus as in claim 71, wherein said tuned horn contains a channel through which said liquid sample flows.

73. An apparatus as in claim 60, wherein said tubular conduit comprises a tuned horn, said tubular conduit comprising a body whose cross sectional area at one end is substantially smaller than the cross sectional area at its other end, so that the amplitude of vibration at the end of said tuned horn of smaller cross sectional area is substantially larger than the amplitude of vibration applied to the end of said tuned horn of larger cross sectional area.

74. An apparatus as in claim 71, wherein said tuned horn comprises an end piece to which said tubular conduit is attached.

75. An apparatus as in claim 74, wherein said end piece is removable from said tuned horn.

76. An apparatus as in claim 75, wherein said end piece is permanently bonded to said tuned horn.

77. An apparatus as in claim 74, wherein said tubular conduit is separable from said end piece.

78. An apparatus as in claim 74, wherein said tubular conduit is permanently bonded to said end piece.

79. An apparatus as in claim 74, wherein said tubular conduit is separably attached to said end piece with a nut and ferrule means.

80. An apparatus as in claim 74, wherein said tubular conduit is separably attached to said end piece with a collet and nut means, said collet means being an integral part of said end piece.

81. An apparatus as in claim 74, wherein said tubular conduit comprises a low dead volume fluid path from the entrance to said tubular conduit located outside the body of said tuned horn to the exit end of said tubular conduit.

82. An apparatus as in claim 74, wherein a continuous channel is formed between said tubular conduit's exit end back through an open bore in said tuned horn, and extending back beyond said tuned horn in a direction opposite to said tubular conduit exit end.

83. A method as in claim 60, wherein said tubular conduit comprises an annular passage around the centermost channel of said tubular conduit, a sheath fluid flowing through said annular passage, said sheath fluid merging with the flow of said liquid sample emerging from the end of said tubular conduit.

84. An apparatus as in claim 71, wherein a case surrounds said tuned horn and extends to near said exit end of said tubular conduit.

85. An apparatus as in claim 84, wherein said case comprises a gap between said tuned horn and said case serving as a gas flow channel with gas entering the back of said case, flowing over said tuned horn, and exiting concentrically near said exit end of said tubular conduit, said case making no contact with the vibrating exit end of said tubular conduit.

86. An apparatus as in claim 60, wherein a vibrating transducer means is directly in contact with said liquid sample and said liquid sample flows into said tubular conduit, so that the vibration of said transducer means is directly imparted to said liquid sample, to vibrate said liquid sample as said liquid sample exits said exit end of said tubular conduit.

87. An apparatus as in claim 60, wherein a vibrating transducer means is coupled to a displaceable element whose surface is in direct contact with said liquid sample, so that vibration is imparted to said liquid sample upstream of said exit end of said tubular conduit, said liquid sample being caused to vibrate as it exits said exit end of said tubular conduit.

88. An apparatus as in claim 60, wherein a vibrating transducer means is coupled to a displaceable element whose surface is in direct contact with a body of liquid of suitable shape, some portion of said body of liquid being in contact with one surface of a thin diaphragm whose other surface is in direct contact with said liquid sample so that vibration is imparted to said liquid sample upstream of said exit end of said tubular conduit, wherein said liquid sample is caused to vibrate as it exits said exit end of said tubular conduit.

89. An apparatus as in claim 65, wherein said tubular conduit is tapered, providing a cross sectional area at the exit end of said tubular conduit that is substantially smaller than the cross sectional area at the inlet end of said tubular conduit, so that the amplitude of vibration of the exit end of said conduit is substantially larger than the amplitude of the vibration provided by said transducer and applied by said transducer to the inlet end of said tubular conduit.

90. An apparatus as in claim 60, wherein said tip of said tubular conduit has a sufficiently small radius of curvature so as to provide an intense electrostatic field at the tip of said tubular conduit when an electrical potential is applied to said tubular conduit.

91. An apparatus as in claim 60, further comprising a bath gas maintained at a substantial fraction of normal atmospheric pressure at sea level for evaporating solvent from said charged liquid droplets to produce said ions.

92. An apparatus as in claim 91, further comprising means for circulating said bath gas countercurrent to the direction of flow of said charged droplets and said ions.

93. A apparatus as in claim 91, further comprising means for directing said bath gas and ions to be analyzed into a vacuum system comprising said analyzer, said mixture of bath gas and molecular ions entering said vacuum system through a tube means of dielectric material whose entrance and exit ends and end faces are electrically conducting so that each end of said tube means can be independently maintained at a desired electrical potential by connection to an electrical power supply mans at said tube entrance end and additional electrical power supply means at said tube exit, each said electrical power supply means having variable voltage.

94. An apparatus as in claim 60, wherein said tubular conduit further comprises
 a first tubular conduit with a small diameter exit end through which said liquid sample solution is introduced form said source and delivered to a desired location in said apparatus, and,
 a second tubular conduit having a bore, through which bore said first tubular conduit extends with means to adjust the relative positions of said first and second tubular conduits' exit ends.

95. A method as in claim 94, wherein said second tubular conduit comprises at least one annular passage through which a sheath fluid flows.

96. A method as in claim 95, wherein said liquid sample and said sheath fluid emerge from said exit ends of said tubular conduits to form a mixture.

97. A method as in claim 96, wherein said second tubular conduit comprises an outermost annular passage and at least one inner annular passage, wherein said sheath fluid flowing in said outermost annular passage comprises a gas.

98. A method as in claim 97, wherein said gas flows at a velocity substantially higher than the velocity of said liquid sample in said channel, wherein said gas exits said outermost annular passage to merge with said liquid sample upon said liquid sample's exit from said exit end of said tubular conduit to nebulize said liquid sample.

99. A method as in claim 97, wherein said nebulizing gas flows at a velocity substantially higher than either the velocity of said liquid sample or said sheath fluid, wherein said nebulizing gas exits said outermost annular passage to merge with said mixture of said liquid sample and said sheath fluid to nebulize said mixture.

100. An apparatus as in claim 94, further comprising a source for said second solution.

101. An apparatus as in claim 94, further comprising a mechanically vibrating transducer coupled to said second tubular conduits so that said exit end of said second tubular conduit can be made to vibrate while solution is flowing through it and while it is being maintained at a high potential relative to said neighboring surface, the combination of said vibration and electric field at said second tubular conduit's exit end serving to disperse said emerging liquid sample into said bath gas as small highly charged droplets which evaporate in said bath gas producing free molecular ions from solute molecules in said sample soution.

102. An apparatus as in claim 94, wherein said first tubular conduit comprises dielectric material.

103. An apparatus as in claim 94, wherein said first tubular conduit comprises a capillary electrophoresis column.

104. An apparatus as in claim 94, wherein said first tubular conduit comprises a conductive material.

105. An apparatus as in claim 94, further comprising means for providing a flow of bath gas in the vicinity of said exit ends of said tubular conduits.

106. An apparatus as in claim 94, further comprising means for directing the flow of said bath gas countercurrent to the flow of said charged droplets after said charged droplets emerge from said tip end of said tubular conduit.

107. An apparatus as in claim 94, wherein said bath gas is provided at a pressure that is a substantial fraction of atmospheric pressure at sea level.

108. An apparatus as in claim 94, further comprising means for analyzing said ions.

109. An apparatus as in claim 108, wherein said analyzing means is in a vacuum system and said bath gas containing said charged droplets and said ions enters the vacuum system through a metal channel that is sufficiently long and sufficiently hot to evaporate said droplets entering the tube.

110. An apparatus as in claim 108, wherein said analyzing means comprises a mass spectrometer.

111. An apparatus as in claim 108, wherein said analyzing means comprises a mobility analyzer.

112. An apparatus as in claim 108, wherein said analyzing means comprises a photon spectrometer.

* * * * *